United States Patent
Britanova et al.

(10) Patent No.: US 11,597,767 B2
(45) Date of Patent: Mar. 7, 2023

(54) MONOCLONAL ANTIBODIES THAT BIND TRBV9 AND METHODS FOR USING SAME FOR INHIBITING THE T CELL RECEPTOR FOR TREATMENT

(71) Applicant: JOINT STOCK COMPANY "BIOCAD", St.Petersburg (RU)

(72) Inventors: Olga Vladimirovna Britanova, Moscow (RU); Mark Aleksandrovic Izraelson, Moscow (RU); Sergey Anatolievich Lukyanov, Moscow (RU)

( * ) Notice: Subject to any disclaimer, the term of this patent is extended or adjusted under 35 U.S.C. 154(b) by 0 days.

(21) Appl. No.: 16/957,328

(22) PCT Filed: Dec. 25, 2018

(86) PCT No.: PCT/RU2018/050168
§ 371 (c)(1),
(2) Date: Sep. 14, 2020

(87) PCT Pub. No.: WO2019/132738
PCT Pub. Date: Jul. 4, 2019

(65) Prior Publication Data
US 2020/0332003 A1    Oct. 22, 2020

(30) Foreign Application Priority Data
Dec. 25, 2017  (RU) .......................... RU2017145662

(51) Int. Cl.
*C07K 16/28* (2006.01)
*A61K 39/395* (2006.01)

(52) U.S. Cl.
CPC ...... *C07K 16/2809* (2013.01); *A61K 39/3955* (2013.01); *C07K 2317/24* (2013.01); *C07K 2317/565* (2013.01); *C07K 2317/73* (2013.01); *C07K 2317/76* (2013.01); *C07K 2317/92* (2013.01)

(58) Field of Classification Search
CPC .. C07K 16/2809; A61K 39/3955; A61P 37/00
See application file for complete search history.

(56) References Cited

FOREIGN PATENT DOCUMENTS

| RU | 2539032 C2 | 1/2015 |
|---|---|---|
| WO | 90/06758 A1 | 6/1990 |
| WO | 94/05801 A1 | 3/1994 |
| WO | 2010/151416 A1 | 12/2010 |
| WO | 2017/137453 A1 | 8/2017 |
| WO | 2017/216324 A1 | 12/2017 |

OTHER PUBLICATIONS

Navid et al, 2012. Seminars in Immunopathology. 43:235-243.*
The related European patent application No. 18895626.2 extended European search report dated Jul. 29, 2021.
Zhijun Liu et al., Prevention of Type 1 Diabetes in the Rat With an Allele-Specific Anti-T-Cell Receptor Antibody. Diabettes, vol. 61, No. 5, May 19, 2012 (May 19, 2012), pp. 1160-1168.
Faham Malek et al., Discovery of T Cell Receptor β Motifs Specific to HLA-B27-Positive Ankylosing Spondylitis by Deep Repertoire Sequence Analysis. Arthritis & Rheumatology (Hoboken), vol. 69, No. 4, Mar. 29, 2017 (Mar. 29, 2017), pp. 774-784.
Medina Frederic et al., Current Practice for Therapeutic Drug Monitoring of Biopharmaceuticals in Spondyloarthritis. Therapeutic Drug Monitoring, vol. 39, No. 4, Aug. 2017 (Aug. 2017), pp. 360-363.
Israelson Ma et al., Testing of monoclonal antibodies against the T-cell receptor associated with ankylosing spondylitis. Preventive Medicine, no. (5)2018, Dec. 1, 2018 (Dec. 1 2018), pp. 71-79.
Baeten D, et al, Secukinumab, an Interleukin-17A Inhibitor, in Ankylosing Spondylitis. N Engl J Med Dec. 24, 2015;373(26):2534-2548.
Kuhn C. and Weiner L., Therapeutic anti-CD3 monoclonal antibodies: from bench to bedside. Immunotherapy Jul. 2016;8(8):889-906.
Helling B et al., A specific CD4 epitope bound by tregalizumab mediates activation of regulatory T cells by a unique signaling pathway. Immunology and Cell Biology Apr. 2015;93(4):396-405.
Konig M. et al., Tregalizumab—A Monoclonal Antibody to Target Regulatory T Cells. Front Immunol Jan. 25, 2016;7:11. pp. 1-7.
Haroon N et al., The Impact of Tumor Necrosis Factor a Inhibitors on Radiographic Progression in Ankylosing Spondylitis. Arthritis Rheum. Oct. 2013;65(10):2645-2654.
Duarte J. et al., Modulation of IL-17 and Foxp3 Expression in the Prevention of Autoimmune Arthritis in Mice. PloS One May 10, 2010;5(5):e10558.
Marie-Paule Lefranc, IMGT, the international ImMunoGeneTics database. Nucleic Acids Research, vol. 29, Issue 1, Jan. 1, 2001, pp. 207-209.
Petersen J et al., Determinants of Gliadin-Specific T Cell Selection in Celiac Disease. J Immunol. 2015; 194(12):6112-22.
Brennan et al., Heterogeneity of T cell receptor idiotypes in rheumatoid arthritis.. Clin Exp Immunol. Sep. 1988; 73(3):417-423.
Taylor L.D. et al. A transgenic mouse that expresses a diversity of human sequence heavy and light chain immunoglobulins. Nucleic Acids Research, vol. 20, Issue 23, Dec. 11, 1992, pp. 6287-6295.
Huston et al. Protein engineering of antibody binding sites: recovery of specific activity in an anti-digoxin single-chain Fv analogue produced in *Escherichia coli*. (1988) Proc. Natl. Acad. Sci. USA 85:5879-5883.

(Continued)

*Primary Examiner* — Zachary C Howard

(57) ABSTRACT

The invention relates to monoclonal antibodies which specifically bind to the TRBV9 family of human T-cell receptors. The invention also relates to a nucleic acid which codes for said antibody or for an antigen-binding fragment thereof, to an expression vector, to a method for producing the antibody, and to the use of said antibody for treating diseases or disorders associated with the family of human T-cell receptors. The invention is directed towards producing antibodies that can be used for eliminating T-cells carrying T-cell receptors of the TRBV9 family, in particular for treating ankylosing spondylitis, coeliac disease, and blood cancers, in the pathogenesis of which T-cell receptors of the TRBV9 family are involved.

13 Claims, 5 Drawing Sheets

Specification includes a Sequence Listing.

(56) References Cited

OTHER PUBLICATIONS

Holliger P. et al. "Diabodies": small bivalent and bispecific antibody fragments. (1993) Proc. Natl. Acad. Sci. USA 90:6444-6448.

Poljak R.J. et al. Production and structure of diabodies. (1994) Structure 2:1121-1123.

Kipriyanov S.M. et al. Single-chain antibody streptavidin fusions: Tetrameric bifunctional scFv-complexes with biotin binding activity and enhanced affinity to antigen (1995) Human Antibodies and Hybridomas 6:93-101.

Colicelli et al., A temperature-sensitive mutation constructed by "linker insertion" mutagenesis. Mol. Gen. Genet. (1985)199:537-539.

Olga V. Britanova et al., Dynamics of Individual T Cell Repertoires: From Cord Blood to Centenarians. J Immunol, 2016, 196(12) 5005-5013.

Van der Heijde D et al., 2010 Update of the international ASAS recommendations for the use of anti-TNF agents in patients with axial spondyloarthritis Annals of the Rheumatic Diseases. Jun. 2011;70(6):905-908.

Turner SJ et al., Structural determinants of T-cell receptor bias in immunity. Nature Reviews Immunology 2006, V.6, 883-894.

Ward et al. Binding activities of a repertoire of single immunoglobulin variable domains secreted from *Escherichia coli*. Nature vol. 341, pp. 544-546 (1989).

Bird et al. Single-chain antigen-binding proteins. (1988) Science 242:423-426.

Kipriyanov S.M. et al. Recombinant single-chain Fv fragments carrying C-terminal cysteine residues: Production of bivalent and biotinylated miniantibodies. (1994) Mol. Immunol., 31:1047-1058.

Barany, Single-stranded hexameric linkers: a system for in-phase insertion mutagenesis and protein engineering. Gene (1985) 37: 111-123.

International application No. PCT/RU2018/050168 International Search Report and its translation with Written Opinion of the International Searching Authority dated May 7, 2019.

Toyabe S et al. "Biclonal expansion of T cells infected with monoclonal Epstein-Barrvims (EBV) in a patient with chronic, active EBV infection", Clinical & Experimental Immunology, vol. 135, Is. 1, Oct. 2003, p. 92-97.

Corresponding Japanese patent application No. 2020-535637 Office Action dated Dec. 9, 2022 (English translations provided).

Yasuto Akiyama et al., Novel approach to the characterization of melanoma associated-peptide-specific CTL lines from Japanese metastatic melanoma patients. International Journal of Oncology (2008), vol. 33, Issue 3, Published online on: Sep. 1, 2008. https://doi.org/10.3892/ijo_00000025. pp. 433-441.

* cited by examiner

MONOCLONAL ANTIBODIES THAT BIND TRBV9 AND METHODS FOR USING SAME FOR INHIBITING THE T CELL RECEPTOR FOR TREATMENT

FIELD OF THE INVENTION

The invention relates to the field of biotechnology and biomedicine, in particular to antibodies or antigen-binding fragments thereof, as well as to use thereof. More specifically, the present invention relates to monoclonal antibodies that specifically bind to a human T cell receptor family. The invention also relates to a nucleic acid encoding said antibody or antigen-binding fragment thereof, an expression vector, a method for preparing said antibody, and use of said antibody in treatment of diseases or disorders associated with the human T cell receptor family.

BACKGROUND OF THE INVENTION

In the treatment of human autoimmune diseases, the use of drugs based on antibodies against the major inflammatory process mediators, such as TNF alpha, IL1, IL6, IL17, IL23 (van der Heijde D et al., Ann Rheum Dis. 2011 June; 70(6):905-8, Baeten D, et al, N Engl J Med. 2015 Dec. 24; 373(26):2534-48). Monoclonal antibodies to CD3 and CD4 receptor complexes, which have immunomodulating properties, are in clinical trials for the treatment of autoimmune diseases, (Kuhn C. and Weiner L., Immunotherapy 2016 July; 8(8):889-906; Helling B. et al., Immunology and Cell Biology 2015 Apr.; 93(4):396-405; Konig M. et al., Front Immunol 2016 Jan. 25; 7:11). However, it has been shown that the use of such drugs, although leading to a decrease in inflammation, does not stop the development of a disease and does not directly act at the cause of the disease, i.e. autoreactive T lymphocytes (Haroon N et al., Arthritis Rheum. 2013 October; 65(10):2645-54., Duarte J. et al., PloS One 2010 May 10 5(5):e10558; Konig M. et al., Front Immunol 2016 Jan. 25; 7:11).

Despite the success of symptomatic treatments of ankylosing spondylitis (AS, Bekhterev's disease) using monoclonal antibodies, an effective drug has not yet been created that allows selective and long-term suppression of autoimmune response and to stop the progression of AS. Thus, it is an urgent task to generate antibodies that allow to rid the AS patients' organism of autoreactive T lymphocyte clones, the emergence of which is associated with the development of the disease.

It is known that the interaction between the antigen-recognizing T cell receptor (TCR) and main histocompatibility complex (MHC, HLA) proteins, which are processed peptides of intracellular proteins or proteins of pathogenic organisms on the surface thereof, plays an important role in the emergence of autoreactive T lymphocyte clones. A number of autoimmune diseases are associated with the presence of a particular HLA gene variant in humans. For example, the HLA-B27 allele is associated with AS, reactive arthritis, and Crohn's disease. The risk of developing autoimmune diseases in carriers of certain HLA allelic variants can be explained by preferential presentation by these alleles of certain peptides that are autoantigens, immune response against which triggers the development of an autoimmune disease. One of the possible mechanisms for the initiation of an autoimmune reaction is the presentation by histocompatibility complex molecules of peptides from proteins of bacterial or viral origin that are homologous to the organism's own peptides, which fact can lead to an immune response against self antigens due to cross-reactivity.

As is known from the prior art, a T cell receptor (TCR) sequence is a marker allowing to identify a T-lymphocytes clone involved in the pathogenesis of an autoimmune disease. Structurally, the subunits of T-cell receptors are members of the immunoglobulin superfamily and are formed from several gene segments. TCR variable regions form the TCR antigen-binding site. This means that they are clone-specific, i.e. differ in T lymphocytes that respond to distinct antigens.

In terms of the amino acid homology of variable (V) gene segments within the TCR variable domain, T cell receptors are divided into different families. According to the IMGT nomenclature, the beta-chain is distinguished into 26 distinct families, and the alpha chain is distinguished into 41 families (Turner Si et al., Nature Reviews Immunology 2006, V.6, 883-894). To determine the TCR chain family, one uses multiple alignment of a test amino acid sequence and known TCR chain sequences, the information on which is summarized in the IMGT database ("The international ImMunoGeneTics information system", Lefranc M-P., Nucl Acids Res 2001; 29:207-209).

A consensus variant of autoimmune TCRs in patients with AS has been described, it has been shown that it is present in synovial fluid and peripheral blood in patients with AS and absent at the same depth of analysis in healthy donors, regardless of their HLA*B27 allele status (Faham M. et al., Arthritis Rheumatol. 2017; 69(4):774-784; Komech E et al. 12th EJI-EFIS Tatra Immunology Conference; 2016 Sep. 3-7; Strbske Pleso, Slovakia. Abstract book p. 39). These TCRs are members of the TRBV9 family (according to the IMGT nomenclature).

It has been shown that T cell receptors bearing TRBV9 family beta-chains are also involved in the development of such an autoimmune disease as celiac disease (Petersen J et al., J Immunol. 2015; 194(12): 6112-22). Also, they are found on the surface of T cells subject to malignization in T cell lymphomas and T cell leukemias, including T-cell lymphoma caused by the Epstein-Barr virus (EBV) (Toyabe S et al., Clin Exp Immunol. 2003; 134(1): 92-97).

The closest analogues of the present invention are the monoclonal antibodies W112 and 2D1 to the beta-chain regions of human T cell receptor variable domains, which belong to TRBV5-3 TRBV8-1 families, which were described in a patent application (WO9006758) as a tool for diagnosis and treatment of rheumatoid arthritis. These monoclonal antibodies recognize between 0.3 to 5% of peripheral T lymphocytes bearing TRBV5-3 and 0.5 to 13% of peripheral T lymphocytes bearing TRBV8-1, respectively. The results of many studies demonstrating the involvement of T lymphocytes in the pathogenesis of rheumatoid arthritis gave rise to the use of monoclonal antibodies specific for T receptors' beta-chain regions. In particular, the data of Brennan et al., Clin Exp Immunol. 1988 September; 73(3): 417-423 has demonstrated elevated percentage of T lymphocytes bearing TRBV5 and TRBV8 in synovial samples of patients suffering from rheumatoid arthritis as compared to healthy donors.

Also, WO9405801 discloses monoclonal antibodies for diagnosis and therapy of rheumatoid arthritis interacting with an epitope of the VB3.1 variable region of human T-cell receptor, which interact with the TCR V(beta)3.1 subfamily.

The main disadvantage of the approaches for treating rheumatoid arthritis described in WO9405801 and WO9006758 is the lack of convincing evidence of a connection between pathogenesis and a particular family of beta-chain variable segment.

Monoclonal antibodies that specifically recognize the 13th family beta-chain of rat TRC have also been described. Animal models has demonstrated that, with the help of these antibodies, it is possible to preventively remove a small population of T cells, the T receptor of which comprises VB13+ beta-chain (VB13+ T cells), and it has been shown that such procedure protects against the development of type I diabetes in rats of type I diabetes-prone line, and also significantly reduces the risk of development of virus-induced diabetes (Zhijun Liu et al., Diabetes. 2012 May; 61(5): 1160-1168.). At the same time, the depletion of T cells, the T receptor of which comprises a distinct beta-chain family (VB16), does not differ in result from control groups. It is important to note that even the first administration of a monoclonal antibody against VB13 results in a 60% decrease in the number of VB13+ T cells in the rat spleen.

All of the described analogues do not bind to TCRs belonging to the TRBV9 family, and are not suitable for treating AS and other diseases associated with TCRs belonging to the TRBV9 family.

Monoclonal antibodies suitable for the elimination of T cells bearing the TRBV9 family TCRs, which antibodies can be used in treating AS and celiac disease, have not been described.

BRIEF DESCRIPTION OF THE INVENTION

The invention is directed to the creation of antibodies, which can be used to eliminate T cells bearing the TRBV9 family TCRs, in particular for the therapy of AS, celiac disease and malignant blood diseases, the pathogenesis of which involves the TRBV9 family TCRs.

The present invention relates to monoclonal antibodies and antigen-binding fragments thereof having the ability to specifically bind to the TRBV9 family beta-chain region of human T receptor. Antibodies according to the invention can be used as a medicine for treating autoimmune and oncological diseases, the pathogenesis of which involves TCRs belonging to the TRBV9 family, for example, AS, celiac disease and some T cell lymphomas and T cell leukemias.

Antibodies and antigen-binding fragments of the present invention are characterized in that 1) the variable domain of heavy chain (VH) thereof comprises 3 hypervariable regions, HCDR1, HCDR2 and HCDR3, wherein
  HCDR 1 (according to the Kabat numbering scheme) has the amino acid sequence of SEQ ID NO: 1;
  HCDR 2 has the amino acid sequence of SEQ ID NO: 2;
  HCDR 3 has an amino acid sequence selected from the group consisting of SEQ ID NO:: 3, SEQ ID NO: 4, SEQ ID NO: 5, SEQ ID NO: 6;
  2) the variable domain of light chain (VL) thereof comprises 3 hypervariable regions, LCDR1, LCDR2 and LCDR3, wherein:
  LCDR 1 has the amino acid sequence of SEQ ID NO:: 7;
  LCDR 2 has the amino acid sequence of SEQ ID NO:: 8;
  LCDR 3 has the amino acid sequence of SEQ ID NO:: 9.

Unless specifically stated otherwise, the well-known Kabat numbering scheme is used hereinafter to determine the CDRs of antibodies.

Antibodies according to the invention can be chimeric, humanized or human antibodies. In some embodiments, the antibodies of the present invention containe human-like constant regions and structural components, but have a rat-like variable domain.

In some embodiments, an antibody light chain variable domain has the amino acid sequence of SEQ ID NO:: 11, and the heavy chain variable domain of the subject antibody has an amino acid sequence selected from the group consisting of SEQ ID NO:: 13, SEQ ID NO:: 15, SEQ ID NO:: 17, SEQ ID NO:: 19.

Also provided is an antibody the amino acid sequence of light chain variable domain of which is substantially similar (e.g., at least 90% identical) to the sequence shown in SEQ ID NO:: 11.

Also provided is an antibody the amino acid sequence of heavy chain variable domain of which is substantially similar (e.g., at least 90% identical) to a sequence selected from the group consisting of SEQ ID NO:: 13, SEQ ID NO:: 15, SEQ ID NO:: 17, SEQ ID NO:: 19.

In some embodiments, an antibody of the invention comprises a light chain, the amino acid sequence of which is substantially similar to SEQ ID NO:: 29, and a heavy chain, the amino acid sequence of which is substantially similar to that selected from the group consisting of SEQ ID NO:: 21, SEQ ID NO:: 23, SEQ ID NO:: 25, SEQ ID NO:: 27.

In some embodiments, monoclonal antibodies of the invention are full-length human IgG antibodies, for example, IgG1 or IgG2 or IgG3 or IgG4.

Also provided are nucleic acids that encode the variable domains of heavy and light chain of an antibody according to the invention, nucleic acids encoding the heavy and light chains of antibodies according to the invention and functional fragments thereof.

Also provided are expression cassettes and expression vectors including a nucleic acid of the present invention and regulatory elements necessary for expression of the nucleic acid in a selected host cell. The vector or expression cassette may be present in the host cell as an extrachromosomal element or integrated into the cell genome as a result of introduction (by transfection) of said expression cassette or vector into the cell.

Furthermore, provided are cells and stable cell lines including nucleic acids, vectors or expression cassettes of the present invention, and methods for preparation thereof.

Also provided is a method for producing the above antibody or antigen-binding fragment thereof, comprising culturing the above host cell in a culture medium under conditions ensuring production of said antibody. In some embodiments, the method includes subsequent isolation and purification of the resulting antibody.

Also provided is a pharmaceutical composition for preventing or treating a disease or disorder mediated by the TRBV9 family beta-chain region of human T receptor, comprising the above antibody or antigen-binding fragment thereof in combination with one or more pharmaceutically acceptable excipients.

In one of embodiments, the pharmaceutical composition is intended to prevent or treat a disease or disorder selected from the group: ankylosing spondylitis, celiac disease, T cell leukemia, T cell lymphoma.

Also provided is a pharmaceutical combination for preventing or treating a disease or disorder mediated by the human T cell receptor bearing the TRBV9 family beta-chain, comprising the above antibody or antigen-binding fragment thereof and at least one other therapeutically active compound.

In one of embodiments, the pharmaceutical combination is intended to prevent or treat a disease or disorder selected from the group: ankylosing spondylitis, celiac disease, T cell leukemia, T cell lymphoma.

In one embodiment, the pharmaceutical combination comprises another therapeutically active compound being selected from a small molecule, antibody or steroid hormones, such as corticosteroids.

Also provided is a method for inhibiting the biological activity of T cell receptor, the beta-chain of which belongs to the TRBV9 family, in a subject in need of such inhibition, comprising administering to the subject an effective amount of the above-mentioned antibody or antigen-binding fragment thereof.

Also provided is a method for treating a disease or disorder mediated by the human T cell receptor bearing the TRBV9 family beta-chain, comprising administering to a subject in need of such treatment the above antibody or antigen-binding fragment thereof or said pharmaceutical composition, in a therapeutically effective amount.

In one of embodiments of the method for treating a disease or disorder, the disease or disorder is selected from the group: ankylosing spondylitis, celiac disease, T cell leukemia, T cell lymphoma.

Also provided is the use of above-mentioned antibody or antigen-binding fragment thereof or above-mentioned pharmaceutical composition for treating in a subject in need of such treatment a disease or disorder mediated by the human T cell receptor bearing the TRBV9 family beta-chain.

In one of embodiments of the use, the disease is selected from the group: ankylosing spondylitis, celiac disease, T cell leukemia, T cell lymphoma.

The technical result of the present invention is to generate novel antibodies, which specifically bind to TCRs, the beta-chain of which belongs to the TRBV9 family, and can be used to treat autoimmune and oncological diseases, the pathogenesis of which involves TCRs, the beta-chain of which belongs to the TRBV9 family. Furthermore, the technical result is to increase the effectiveness of treatment of AS and/or celiac disease, which increase is provided by producing antibodies capable of acting directly on autoimmune T lymphocytes, and to achieve prolonged remission in AS.

DETAILED DESCRIPTION OF THE INVENTION

Figure 1:
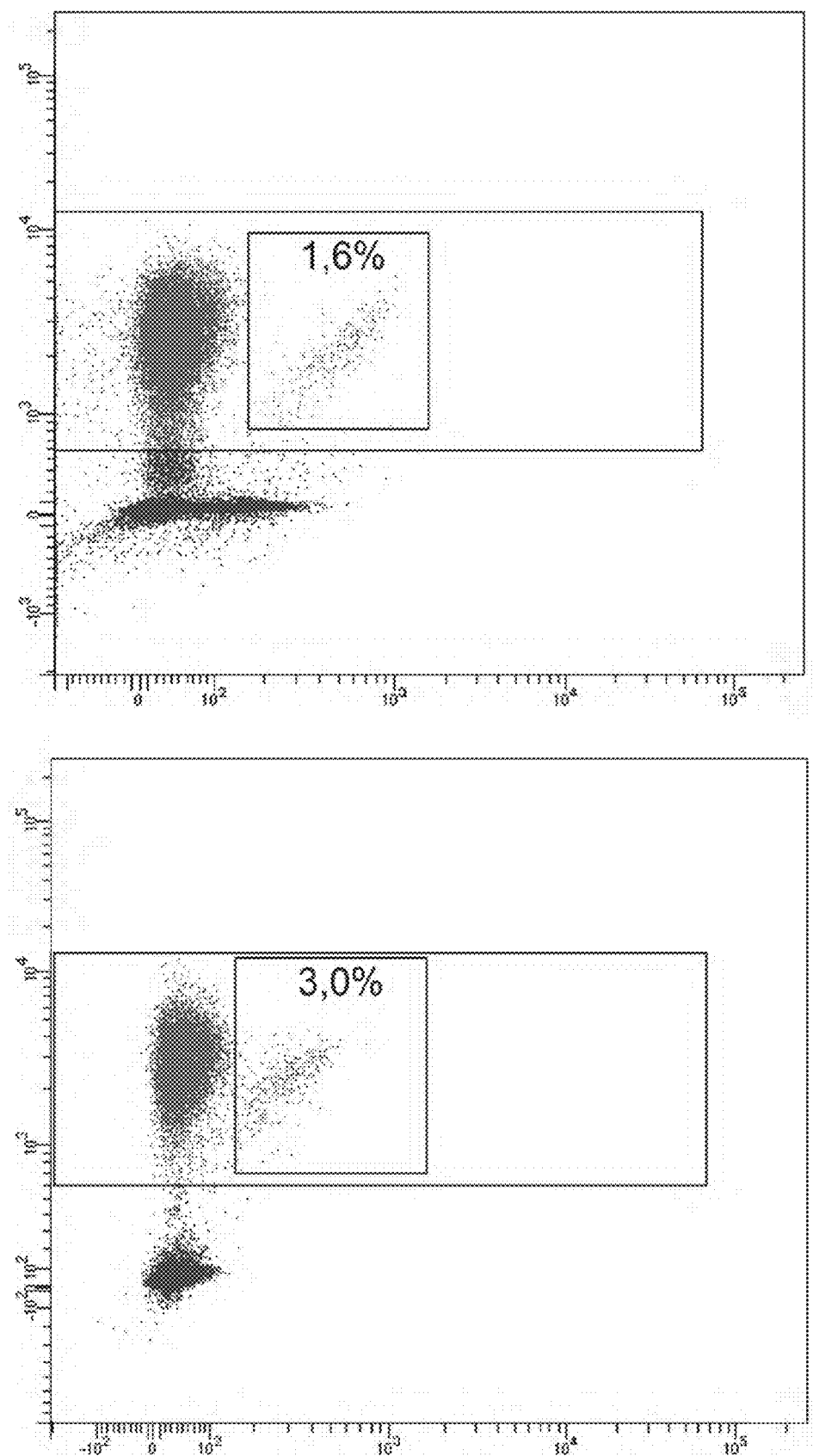
FIGS. 1-4 show two-parameter histograms of distribution of mononuclear blood fraction cells using anti-CD3 monoclonal antibody (ordinate axis) labeled with eFluor 405 and monoclonal antibodies against TRBV9 (abscissa axis) labeled with FITC: anti-TRBV9-1 (FIG. 1), anti-TRBV9-2 (FIG. 2), anti-TRBV9-3 (FIG. 3), anti-TRBV9-4 (FIG. 4). Each variant of the anti-TRBV9 monoclonal antibody was used in two concentrations: 270 ng (upper graph) or 27 ng (lower graph) per test. The small rectangle denotes the specific population of CD3+TRBV9+.
Figure 2:
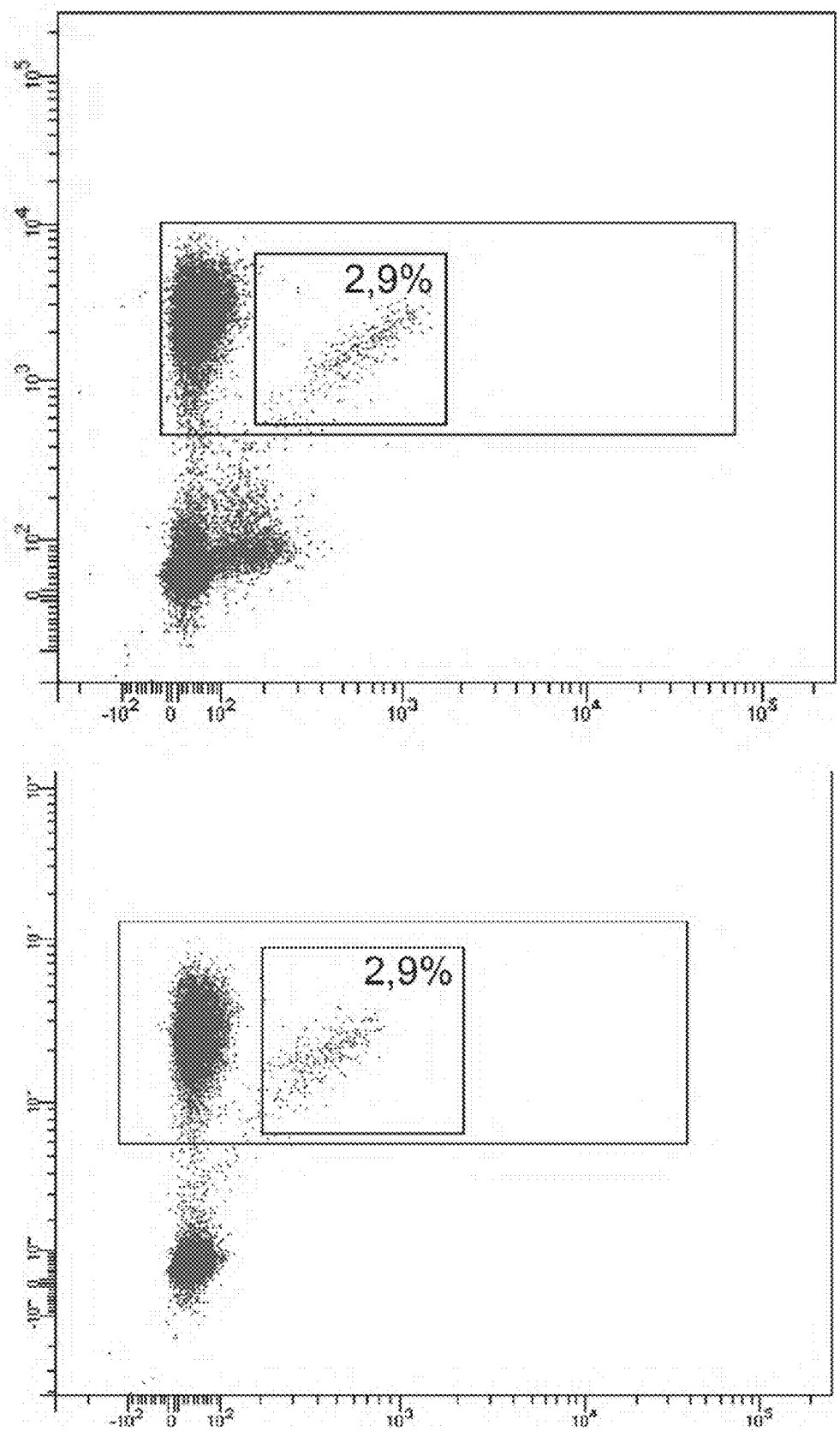
Figure 3:
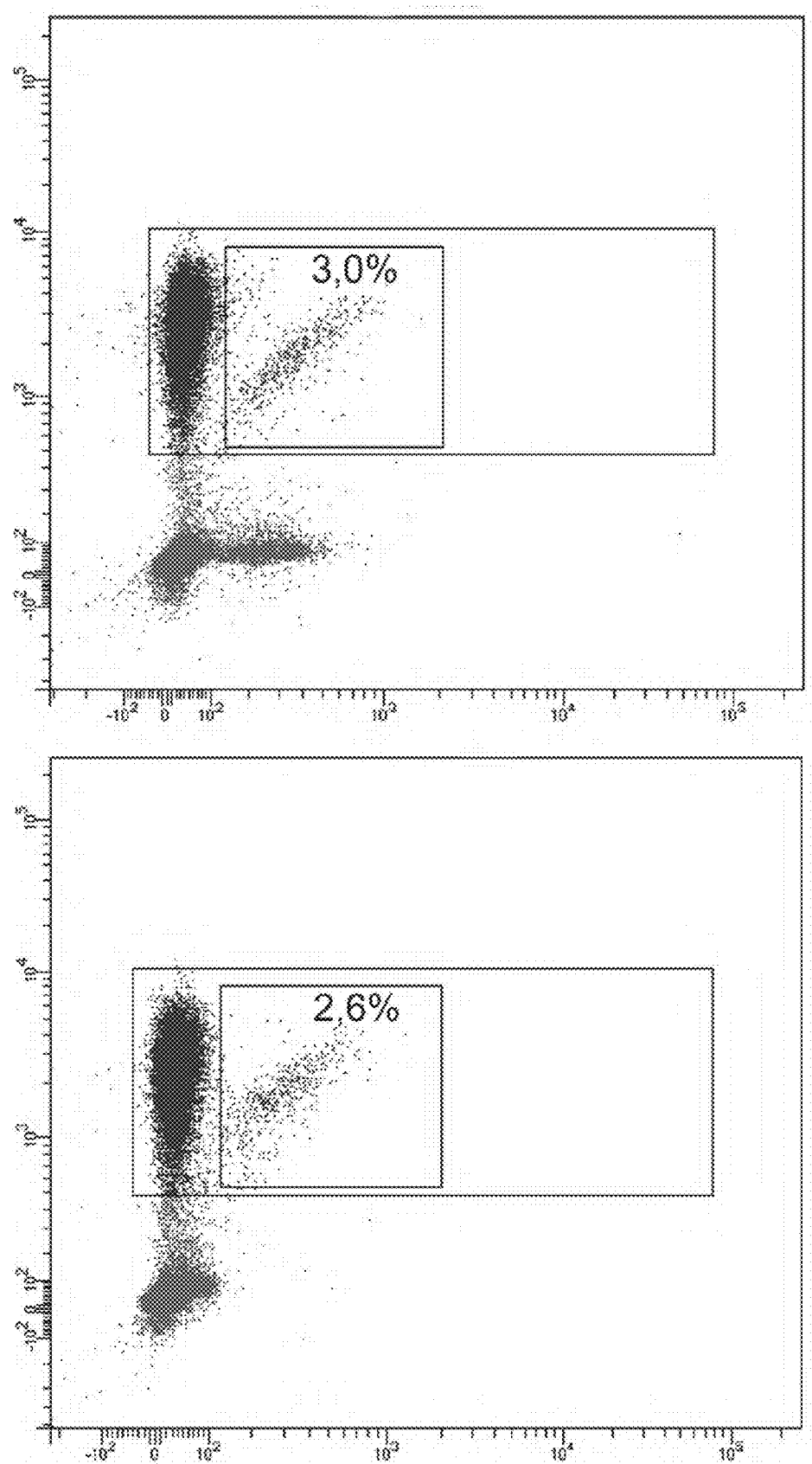
Figure 4:
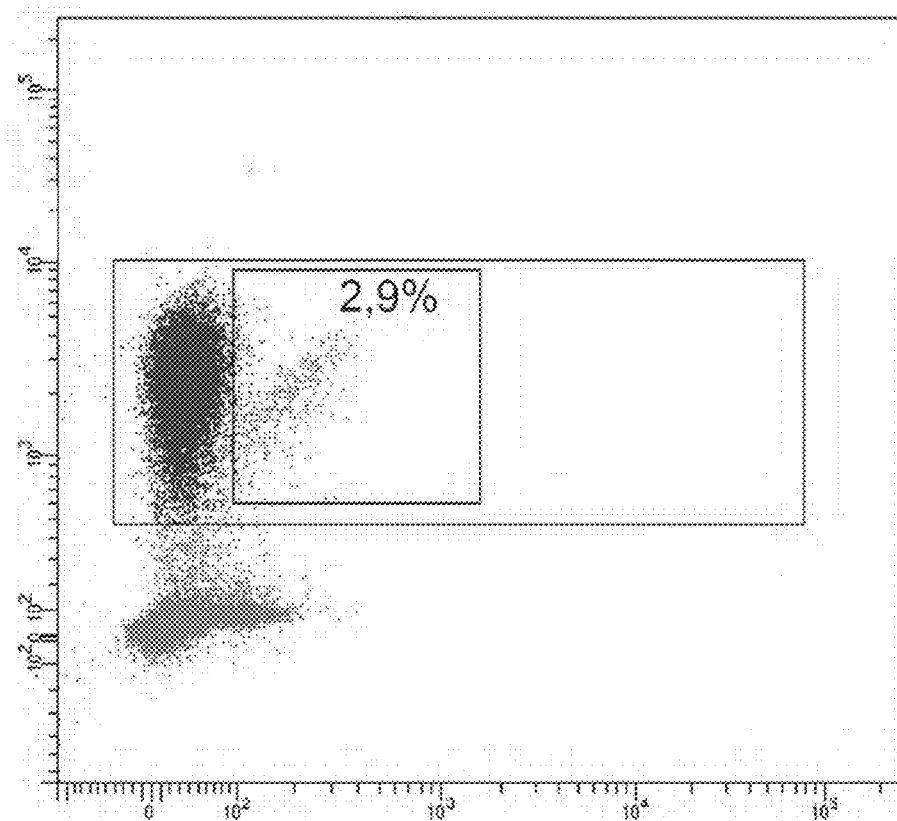
Figure 4:
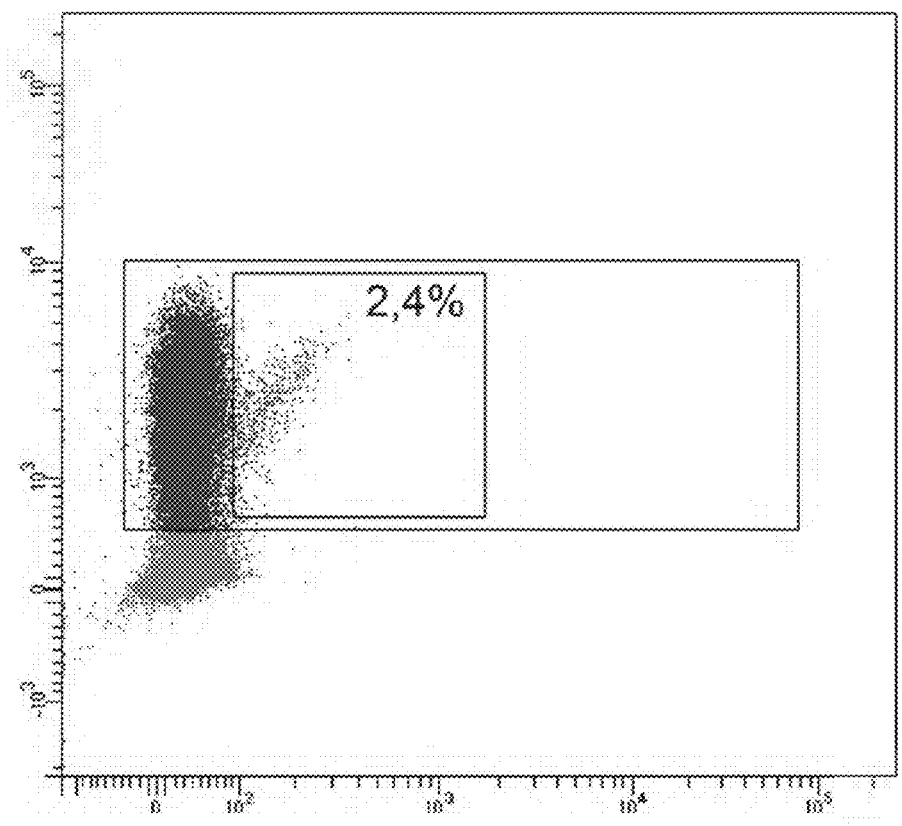

The present invention relates to isolated monoclonal antibodies and functional fragments thereof having the ability to specifically bind to the TRBV9 family beta-chain region of human T receptor. Also provided are nucleic acids encoding antibodies and fragments thereof of the invention, expression cassettes and expression vectors including a nucleic acid of the present invention and regulatory elements necessary for expression of the nucleic acid in a selected host cell. Furthermore, provided are cells and stable cell lines including nucleic acids, vectors or expression cassettes of the present invention. Also provided are a method for producing a monoclonal antibody or a functional fragment thereof, a pharmaceutical composition and a pharmaceutical combination comprising in an effective amount an antibody of the present invention in combination with one or more pharmaceutically acceptable excipients, diluents or carriers, and methods for diagnosis and therapy of AS and other diseases using antibodies of the present invention.

Definitions

The invention will be easier understood with definition of some terms first.

It is understood that the materials and methods provided herein are not limited to particular compositions and method steps, as these may vary. It must be noted that as used herein and in the appended claims, the singular forms include the corresponding plural reference unless the context clearly dictates otherwise.

Human "T cell receptor", also referred to as "TCR", "T receptor", is a heterodimeric protein complex found on the surface of a T lymphocyte. This receptor is present only on T lymphocytes. The main function of TCR is to specifically recognize processed antigens bound to the molecules of major histocompatibility complex (HLA).

Human TCR consists of two subunits, a and beta-chains, or γ and δ chains, connected through a disulfide bond and docked onto the cell membrane. Each of the TCR chains has an N-terminal variable (V) domain, a connecting domain, and a constant (C) domain connected to a transmembrane domain that anchors the receptor in the T lymphocyte plasma membrane. The length of the constant domain of alpha and beta-chains is 91 and 129 amino acid residues, respectively. The length of the connecting and transmembrane domain of the alpha chain is 30 and 17 amino acid residues (AARs), and that of the beta-chain is 21 and 22 AARs. The length of T receptors variable domains varies from 104 to 125 AARs.

A small fraction of T lymphocytes has the γ/δ type receptors. They are arranged similar to the α/β receptors, but differ in their primary structure and have a number of functional features. They exhibit a much lower variability (limited clone specificity), they recognize antigens in the complex with "non-classical" (non-MHC) antigen-presenting molecules or even free antigens.

The T receptor reacts with the MHC/antigen complex via six regions determining complementarity thereof (CDRs): three alpha chain regions and three beta-chain regions. These CDRs are hypervariable regions, the loops of variable domains of the T cell receptor, Valfa and Vbeta.

The terms "TRBV9" or "TRBV9 family" refer to the ninth family of beta-chains of T cell receptors, as distinguished according to the IMGT nomenclature, which is characterized in that the amino acid sequence of variable domain thereof comprises unique motifs of CDR1 (amino acid sequence is S-G-D-L-S) and CDR2 (amino acid sequence is Y-Y-N-G-E-E). The term "TRBV9 family TCR" refers to a T cell receptor, the beta-chain of which belongs to the TRBV9 family.

The term "pathological" in relation to T lymphocytes or TCRs means that such TCR or a TCR-bearing T lymphocyte are associated with a disease or pathology and/or cause a disease and/or contribute to the development of a disease.

The term "autoimmune" in relation to TCR means that such TCR is involved in the development of an autoimmune disease.

The term "antibody" as used herein is intended to refer to an immunoglobulin molecule consisting of four polypeptide chains (two heavy (H) chains and two light (L) chains) linked by disulfide bonds. Light chains are classified as kappa or lambda. Heavy chains are classified as gamma, mu, alfa, delta or epsilon; they determine the antibody isotype such as IgG, IgM, IgA, IgD and IgE respectively, and several of them can be further divided into subclasses (isotypes), for example IgG1, IgG2, IgG3, IgG4, IgA1 and IgA2. Each heavy chain type is characterized by a specific constant region.

Each heavy chain comprises a heavy chain variable region (herein abbreviated as HCVR or VH) and a heavy chain constant region. The heavy chain constant region comprises three domains, CH1, CH2, and CH3. Each light chain comprises a light chain variable region (herein abbreviated as LCVR or VL) and a light chain constant region. The light chain constant region comprises one domain, CL. The VH and VL regions can be further subdivided into regions of hypervariability, termed complementarity determining regions (CDRs), surrounded by regions that are more conserved, termed framework regions (FRs). Each VH and VL is composed of three CDRs and four FRs, arranged from amino-terminus to carboxy-terminus in the following order: FR1, CDR1, FR2, CDR2, FR3, CDR3, FR4.

In the present application, 3 heavy chain CDRs are referred to as "CDRH1, CDRH2 and CDRH3", whereas 3 light chain CDRs are referred to as "CDRL1, CDRL2 and CDRL3". The CDRs contain most of residues that specifically interact with the antigen. CDR-amino residues within HCVRs and LCVRs of antibodies according to the present invention are numbered and positioned in compliance with the well-known Kabat numbering scheme, unless otherwise stated. The present application includes the conventional letter codes for amino acids, unless otherwise stated.

The terms "anti-TRBV9 antibody", "antibody to TRBV9", "antibody specifically binding to the TRBV9 family beta-chain" and "antibody against the TRBV9 family beta-chain" are interchangeable in the context of the present application and relate to an antibody that specifically binds to the epitope of TRBV9 family beta-chain of human T cell receptor.

The terms "antibody" and "monoclonal antibody" for the purposes of the present application refer to a monoclonal antibody against the TRBV9 family TCR. As used herein, "monoclonal antibody" relates to an antibody of rodents, primates or Camelidae family, preferably to a mouse, macaque, camel or llama antibody, chimeric antibody, humanized antibody or fully human antibody, unless otherwise stated.

The variable regions of each pair light/heavy chain form antigen-binding sites of antibody. As used in this application, an "antigen binding portion", or "antigen binding region", or "antigen binding domain" or "antigen-binding site" interchangeably relate to such portion of an antibody molecule which comprises amino acid residues which interact with the antigen and give the antibody specificity and affinity in relation to the antigen. This portion of antibody includes "framework" amino acid residues needed to maintain appropriate conformation of antigen-binding residues.

The term "human antibody", as used herein, refers to an antibody, in which the sequences of variable and constant domains are derived from human sequences. Human antibodies according to the invention may include amino acid residues that are not typical of human (for example, mutations introduced by in vitro undirected or site-specific mutagenesis or in vivo somatic mutation), for example, in CDR, and particularly, in CDR3.

The term "humanized", when used in reference to antibodies, is used to refer to antibodies that are characterized by the presence of human-like constant regions and structural components, but have complementarity determining regions (CDRs) that are typical of immunoglobulins of other origin, or of corresponding fragments of modified antibodies.

The term "chimeric" in reference to antibodies of the present invention is used to refer to antibodies that are characterized by human-like constant regions but have variable regions of other origin. In such antibodies, the variable domains of light and/or heavy chains of non-human origin (for example, of rat origin) are operatively linked to the constant domains of the corresponding chains of human origin.

The term "operatively linked" or the like, when used to describe antibodies, refers to polypeptide sequences that are placed in a physical (covalent, unless stated otherwise) and functional relationship to each other. In the most preferred embodiments, the functions of the polypeptide components of the chimeric molecule are unchanged as compared to the functional properties of isolated polypeptide components. The term "operatively linked" or the like, when used to describe nucleic acids, means that the nucleic acids are covalently linked so that no reading frame shifts and stop codons are present at the points where they are linked. As is obvious to those skilled in the art, nucleotide sequences encoding a chimeric protein comprising "operatively linked" components (proteins, polypeptides, linker sequences, protein domains, etc.) consist of fragments encoding said components, wherein said fragments are covalently linked so that a full-length chimeric protein, for example, a chimeric antibody according to the invention, is produced during translation and transcription of the nucleotide sequence.

As used herein, the term "isolated" or "derived" mean a molecule or a cell that are in an environment other than that in which the molecule or the cell exist in nature.

In preferred embodiments, antibodies of the present invention are recombinant, i.e. generated using the recombinant DNA technique. The term "recombinant antibody", as used herein, includes all antibodies that are prepared, expressed, created or isolated by recombinant means, such as antibodies expressed using a recombinant expression vector introduced into a host cell, antibodies isolated from recombinant, combinatorial human antibody library, antibodies isolated from an animal that is transgenic for human immunoglobulin genes (see, e.g., Taylor L. D. et al. (1992) Nucl. Acids Res. 20:6287-6295). In some embodiments, the recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "specifically binds" as used herein is intended to refer to the situation in which one member of a specific binding pair does not significantly bind to molecules other than specific binding partner(s) thereof. The term is also applicable where e.g. an antigen-binding domain of an antibody of the invention is specific for a particular epitope that is carried by a number of antigens; in this case, the specific antibody comprising the antigen-binding domain will be able to specifically bind to various antigens carrying the epitope. Accordingly, the monoclonal antibody of the invention specifically binds the epitope of TRBV9 family beta-chain of human T cell receptor, whereas it does not specifically bind the TCR beta-chains of other families and TCR alpha chains.

The term "epitope" refers to that portion of a molecule capable of being recognized by and bound by an antibody at one or more of the antibody's antigen-binding regions. Epitopes often consist of a chemically active surface grouping of molecules such as amino acids or sugar side chains and have specific three-dimensional structural characteristics as well as specific charge characteristics.

As used in this application, the term "epitope", inter alia, refers to a polypeptide fragment, having antigenic and/or immunogenic activity in an animal, preferably in a mammal, for example a mouse, rat or human. The term "antigenic epitope" as used herein is a polypeptide fragment which can specifically bind the antibody and can be detected by any technique well known from the prior art, for example, by the standard immunoassay. Antigen epitopes are not necessarily immunogenic, however, they can be immunogenic. "Immunogenic epitope" as used herein is defined as a polypeptide fragment that evokes an antibody response in an animal, as determined by any method known from the prior art. "Non-linear epitope" or "conformational epitope" comprise non-adjacent polypeptides (or amino acids) within an antigen protein that binds to epitope-specific antibody.

The term "biological property" or "biological characteristic", or the terms "activity" or "bioactivity" in reference to an antibody or functional fragments thereof of the present invention are used interchangeably in this application and include, but are not limited to, epitope/antigen affinity and specificity, ability to neutralize or antagonize the activity of TCR that includes a beta-chain belonging to the TRBV9 family.

Other identifiable biological properties or characteristics of the antibody include, for example, cross-reactivity, (i.e., with non-human homologs of a target peptide, or with other proteins or tissues, generally), and ability to preserve high levels of expression of protein in mammalian cells. The aforementioned properties or characteristics can be observed, measured, and/or assessed using techniques recognized in the art including, but not limited to, ELISA, competitive ELISA, KINEXA surface plasmon resonance analysis, in vitro or in vivo inhibition assays without limitation, receptor binding assays, cytokine or growth factor production and/or secretion assays, and signal transduction and immunohistochemistry of tissue sections obtained from various sources, including human, primate or any other source.

The terms "inhibit" or "neutralize" as used herein with respect to the activity of an antibody of the invention refer to the ability to substantially antagonize, prohibit, prevent, restrain, slow, disrupt, eliminate, stop, reduce, for example progression or severity of that which is being inhibited including, but not limited to, the biological activity of antibody, or property, disease or condition.

As used herein, the term "mutant" or "variant" refers to an antibody disclosed in the present invention, in which one or more amino acids are added and/or substituted and/or deleted and/or inserted at the N-terminus and/or C-terminus and/or within the native amino acid sequences of antibodies of the present invention or fragments thereof. As used herein, the term "mutant" also refers to a nucleic acid molecule that encodes a mutant protein. Furthermore, the term "mutant" refers to any variant that is shorter or longer than the protein or nucleic acid.

The term "homology" is used to describe the relationship of nucleotide or amino acid sequences with other nucleotide or amino acid sequences, which is determined by the degree of identity and/or similarity between said sequences being compared.

As used herein, an amino acid or nucleotide sequence are "substantially similar" or "substantially the same" as a reference sequence if the amino acid or nucleotide sequence has at least 70% identity with a specified sequence within a region selected for comparison. Thus, substantially similar sequences include those that have, for example, at least 75% identity, for example at least 80% identity, at least 85% identity, at least 90% identity (for example, 90%, 91%, 92%, 93%, 94%, 95%, 96%, 97%, 98%, 98% or 99% identity). Two sequences that are identical to one another are also substantially similar.

The sequence identity is determined based on a reference sequence. Algorithms for sequence analysis are known in the art, such as IgBLAST described in Ye et al. Nucleic Acids Res. 2013, W34-40. For the purposes of the present invention, to determine the level of identity and similarity between nucleotide sequences and amino acid sequences, the nucleotide and amino acid sequences can be compared with the help of IgBLAST software package provided by the National Center for Biotechnology Information using gapped alignment with standard parameters. To calculate the percent identity, the full length of the reference sequence, for example, a variable region, is used.

The reference to a nucleotide sequence "encoding" polypeptide means that the polypeptide is produced from the nucleotide sequence during translation and transcription of mRNA. Thereby, both a coding chain identical to mRNA and typically used in the list of sequences and a complementary chain that serves as a template for transcription can be indicated. As is obvious to those skilled in the art, the term also includes any degenerate nucleotide sequences encoding the same amino acid sequence. The nucleotide sequences encoding the polypeptide include sequences comprising introns.

Antibodies

As mentioned above, the present invention relates to isolated monoclonal antibodies and functional fragments thereof having the ability to specifically bind to the TRBV9 family beta-chain region of human T receptor.

Antibodies according to the invention are characterized in that a) a variable domain of heavy chain (VH) thereof comprises 3 hypervariable regions, HCDR1, HCDR2 and HCDR3, wherein Antibodies of the present invention are characterized in that a) a variable domain of heavy chain (VH) thereof comprises 3 hypervariable regions, HCDR1, HCDR2 and HCDR3, wherein HCDR1 (according to the Kabat numbering scheme) has the amino acid sequence DYLVH (SEQ ID NO: 1);

HCDR2 has the amino acid sequence WINTYTGTPTY-ADDFEG (SEQ ID NO: 2);

HCDR3 has an amino acid sequence selected from the group consisting of SWRRGLRGLGFDY (SEQ ID NO: 3), SWRRGLRGIGFDY (SEQ ID NO: 4), SWRRGIR-GLGFDY (SEQ ID NO: 5), SWRRGIRGIGFDY (SEQ ID NO: 6);

b) a variable domain of light chain (VL) thereof comprises 3 hypervariable regions, LCDR1, LCDR2 and LCDR3, wherein:

LCDR1 has the amino acid sequence KASKSINKYLA (SEQ ID NO: 7);

LCDR2 has the amino acid sequence DGSTLQS (SEQ ID NO: 8);

LCDR3 has the amino acid sequence QQHNEYPPT (SEQ ID NO: 9).

Antibodies according to the invention can be chimeric, humanized or human antibodies, or antigen-binding fragments thereof, and can be used as a medicine for treating Bekhterev's disease and other diseases, the pathogenesis of which involves TCRs belonging to the TRBV9 family, for example, celiac disease or T cell lymphoma.

The monoclonal antibodies of the invention can be obtained using, for example, hybridoma techniques well known in the art, as well as recombinant technologies, phage display technologies, synthetic technologies or combinations of such technologies or other technologies well known in the art. The term "monoclonal antibody" as used in this application refers to an antibody obtained from a single copy or a clone including, for example, any eukaryotic, prokaryotic or phage clone, rather than to production method thereof.

Humanized and chimeric antibodies can be obtained by peptide synthesis or using recombinant DNA techniques as described in the "Nucleic acids" section below.

In some embodiments, antibodies of the present invention are chimeric and characterized in that they have variable domains of light and heavy chains of non-human origin (for example, of rat or mouse), and human origin constant domains. In some embodiments, the antibodies of the present invention are characterized in that they have the amino acid sequence of heavy chain variable domain selected from the group of SEQ ID NO: 13, SEQ ID NO: 15, SEQ ID NO: 17, SEQ ID NO: 19, and the amino acid sequence of light chain variable domain shown in SEQ ID NO: 11. Thereby, in preferred embodiments, the antibody comprises the constant region of heavy chain, such as the constant region of human IgG1, IgG2, IgGS, IgG4, IgA, IgE, IgM, IgD. Preferably, the heavy chain constant region is a human IgG1 heavy chain constant region. Furthermore, an antibody may comprise either a light chain constant region or a light chain kappa constant region or a light chain lambda constant region. Preferably, the antibody comprises a light chain kappa constant region.

Examples of the amino acid sequences of heavy chains of anti-TRBV9-1, anti-TRBV9-2, anti-TRBV9-3 or anti-TRBV9-4 antibodies according to the invention are shown in SEQ ID NO: 21, 23, 25 and 27, respectively. An exemplary amino acid sequence of light chain of an antibody is shown in SEQ ID NO: 29.

In some embodiments, the amino acid sequences of framework regions of variable domains of an antibody, or portions thereof, are generally of human origin and, therefore, are "humanized antibodies". This "humanization" is considered useful in reducing the immunogenicity of said antibody for therapeutic use in patients. Certain selected amino acid residues in framework regions remain rat, rather than human.

In some embodiments, antibodies of the present invention and antigen-binding fragments thereof include variable domains of light chains, the amino acid sequences of which are substantially similar to that of SEQ ID NO: 11, for example, are at least 90% identical, more often at least 93% identical, typically 94% or more identical (preferably 95% or more identical, 96% or more identical; 97% or more identical, 98% or more identical, 99% or more identical, or 99.5% or more identical).

In some embodiments, antibodies of the present invention and antigen-binding fragments thereof include variable domains of heavy chains, the amino acid sequences of variable domains of which are substantially similar to that selected from the group of SEQ ID NO: 15, SEQ ID NO: 17, SEQ ID NO: 19. For example, they have an amino acid sequence that is at least 90% identical, more often at least 93% identical, typically 94% or more identical (preferably 95% or more identical, 96% or more identical; 97% or more identical, 98% or more identical, 99% or more identical or 99.5% or more identical) to that selected from the group of SEQ ID NO: 13, SEQ ID NO: 15, SEQ ID NO: 17, SEQ ID NO: 19.

In some embodiments, an antibody of the present invention includes a heavy chain having an amino acid sequence that is at least 90% identical (e.g., 93% or more identical, 94% or more identical, 95% or more identical, 96% or more identical; 97% or more identical, 98% or more identical, 99% or more identical, or 99.5% or more identical) to that selected from the group consisting of SEQ ID NO: 21, SEQ ID NO: 23, SEQ ID NO: 25, SEQ ID NO: 27 and a light chain having an amino acid sequence that is at least 90% identical (e.g., 93% or more identical, 94% or more identical, 95% or more identical, 96% or more identical; 97% or more identical, 98% or more identical, 99% or more identical or 99.5% or more identical) to that of SEQ ID NO: 29.

As is known from the prior art, mutations can be introduced into antibody sequences, including variable domains, which do not substantially alter the antibody ability to bind to an antigen. Antibodies of the present invention may also comprise further mutations that do not lead to a loss in the antibody ability to bind the TRBV9 family beta-chain of TCR, but can lead to a decrease in antibody-dependent cell-mediated cytotoxicity or an increase in affinity or other biological properties of antibodies. In particular, as is well known from the prior art, conservative amino acid substitutions can be made in an antibody sequence. "Conservative substitution", as used in this application, means a substitution in which an amino acid residue is substituted by another amino acid residue having a similar side chain. Families of the amino acid residues having similar side chains are well-known in the art, which include basic side chains (e.g., lysine, arginine, histidine), acidic side chains (e.g., aspartic acid, glutamic acid), non-charged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), (3-branched side chains (e.g., threonine, valine, isoleucine), and aromatic side chains (e.g., tyrosine, phenylalanine, tryptophan, histidine). Preferably, CDR3 regions in the VL and/or VH domains include no more than five conservative amino acid substitutions, more often no more than three conservative substitutions. Typically, conservative substitutions are not made at amino acid positions that are critical for binding the epitope of the TRBV9 family beta-chain.

The above variants (mutants) of antibodies according to the invention can be generated by peptide synthesis or using recombinant DNA techniques as described in the "Nucleic acids" section below.

Also provided are antigen-binding fragments of antibodies of the present invention. The term "antigen-binding fragment" of an antibody (or "functional fragment of an antibody" or "active fragment of an antibody"), as used herein, refers to one or more antibody fragments that retain the ability to specifically bind an antigen. It has been shown that the antigen-binding function of an antibody can be performed by fragments of a full-length antibody. Examples of binding fragments encompassed within the term "antigen-binding portion" of an antibody include (a) a Fab fragment, a monovalent fragment consisting of VL, VH, CL and CH1 domains; (b) a F(ab)2 fragment, a bivalent fragment comprising two Fab fragments linked by a disulfide bridge at the hinge region; (c) a Fd fragment consisting of VH and CH1 domains; (d) a Fv fragment consisting of VL and VH domains of a single arm of an antibody; (e) a dAb fragment (Ward et al. (1989) Nature 341:544-546) that consists of a VH domain, and (f) an isolated complementarity determining region (CDR). Furthermore, although the two domains of the Fv fragment, VL and VH, are encoded by separate genes, they can be linked, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; Huston et al. (1988) Proc. Natl. Acad. Sci. USA 85:5879-5883). Such single chain antibodies are also contemplated to be encompassed within the term "antigen-binding fragment" of an antibody. They also include other forms of single chain antibodies, such as diabodies. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger P. et al. (1993) Proc. Natl. Acad. Sci. USA 90:6444-6448; Poljak R. J. et al. (1994) Structure 2:1121-1123).

Antibody fragments, such as Fab and F(ab')2, may be obtained from whole antibodies using conventional techniques, such as papain or pepsin digestion, respectively, of whole antibodies. Moreover, antibodies, antibody fragments and immunoadhesion molecules can be obtained using standard recombinant DNA techniques.

The antibody or antigen-binding portion thereof may be part of larger immunoadhesion molecules formed by covalent or noncovalent association of the antibody or antibody fragment with one or more protein or peptide. Examples of such immunoadhesion molecules include use of a streptavidin core region to make a tetrameric scFv molecule (Kipriyanov S. M. et al. (1995) Human Antibodies and Hybridomas 6:93-101) and use of a cysteine residue, a marker peptide and a C-terminal polyhistidine tag to make bivalent and reduced-size scFv biomolecules (Kipriyanov S. M. et al. (1994) Mol. Immunol., 31:1047-1058). Other chemical bonds between antibody fragments are also well known from the state of art.

The antibodies and functional fragments thereof according to the invention are present in an isolated form, i.e. this means that such a protein is substantially free from the presence of other proteins or other naturally occurring biological molecules, such as oligosaccharides, nucleic acids and fragments thereof, etc., wherein the term "substantially free" in this case means that less than 70%, typically less than 60%, and more often less than 50% of said composition comprising the isolated protein is other naturally occurring biological molecule. In some embodiments, said proteins are present in substantially purified form, wherein the term "substantially purified form" means a purity equal to at least 95%, typically equal to at least 97%, and more often equal to at least 99%.

Methods for purifying an antibody obtained by recombinant or hybridoma techniques are well known in the art, for example, purification can be performed by chromatography (for example, ion exchange chromatography, affinity chromatography, especially affinity for the specific antigens Protein A or Protein G, and sizing column chromatography), centrifugation, differential solubility, or any other standard technique for purifying proteins. Furthermore, antibodies generated by the technology according to the present invention or fragments thereof can be fused to heterologous polypeptide sequences (e.g., a histidine tag) to facilitate purification.

The antibody affinity can be determined using the standard analysis by determining dissociation constants (KD). KD is calculated using the equation KD=kd/kon, where kd is the experimentally calculated dissociation rate constant and kon is the experimentally calculated association rate constant of the antibody-antigen complex.

Preferred antibodies are those that bind a human antigen with a KD value of not more than about $1\times10^{-7}$ M; preferably not more than about $1\times10^{-8}$ M; more often not more than about $1\times10^{-9}$ M; more preferably not more than about $1\times10^{-10}$ M, and most preferably not more than about $1\times10^{-11}$ M, for example, not more than about $1\times10^{-12}$ M.

Preferred antibodies include anti-TRBV9-1, anti-TRBV9-2, anti-TRBV9-3 or anti-TRBV9-4, characterized by CDR3 sequence and described in detail in the experimental section below.

Antibodies and fragments thereof that can be used in the present compositions and methods are biologically active antibodies and fragments, i.e. they are capable of binding the desired antigenic epitopes and exhibiting the biological effect directly or indirectly.

Antibodies and functional fragments thereof according to the invention are able to specifically bind the epitope (region) of the TRBV9 family beta-chain. In preferred embodiments, specific binding thereof to the TRBV9 family beta-chain results in inhibited activity of TCRs that include said beta-chain. Typically, inhibition is preferably at least about 20, 30, 40, 50, 60, 70, 80, 90, 95% or more.

In some embodiments, an antibody against the TRBV9 family beta-chain according to the invention or a fragment thereof can eliminate T cells bearing TCR comprising the TRBV9 family beta-chain. In some embodiments, an antibody or fragment thereof according to the invention can provide at least about 20%, at least about 30%, at least about 40%, at least about 50%, at least about 60%, at least about 70%, at least about 80%, at least about 90%, at least about 95%, or about 100% elimination of T lymphocytes.

Nucleic Acids

The present invention provides nucleic acid molecules encoding the heavy and light chains of the antibody of the present invention, the functional fragments and variable domains thereof, which can be used to produce chimeric antibodies including the variable domains of the invention operatively fused with the known constant domains of human antibodies.

In preferred embodiments, a nucleic acid of the invention encodes an antibody heavy chain, the variable domain of which comprises 3 hypervariable regions, HCDR1, HCDR2 and HCDR3, wherein HCDR1 (according to the Kabat numbering scheme) has the amino acid sequence of SEQ ID NO: 1;

HCDR2 has the amino acid sequence of SEQ ID NO: 2;

HCDR3 has an amino acid sequence selected from the group consisting of SEQ ID NO:: 3, SEQ ID NO: 4, SEQ ID NO: 5, SEQ ID NO: 6;

In preferred embodiments, a nucleic acid of the invention encodes an antibody light chain, the variable domain of which comprises 3 hypervariable regions, LCDR1, LCDR2 and LCDR3, wherein:

LCDR1 has the amino acid sequence of SEQ ID NO: 7;

LCDR2 has the amino acid sequence of SEQ ID NO: 8;

LCDR3 has the amino acid sequence of SEQ ID NO: 9.

The nucleic acid molecules encoding the homologs and mutants of said antibody chains, functional fragments and domains thereof are also within the scope of the present invention.

In some embodiments, nucleic acid encodes an antibody light chain, the variable domain of which comprises an amino acid sequence that is substantially similar to that of SEQ ID NO: 11; for example, they are at least 90% identical, more often at least 93% identical, typically 94% or more identical (preferably 95% or more identical, 96% or more identical; 97% or more identical, 98% or more identical, 99% or more identical, or 99.5% or more identical).

In some embodiments, nucleic acid encodes an antibody heavy chain, the variable domain of which comprises an amino acid sequence that is substantially similar to that selected from the group consisting of SEQ ID NO: 13, SEQ ID NO: 15, SEQ ID NO: 17, SEQ ID NO: 19; for example, they are at least 90% identical thereto, more often at least 93% identical, typically 94% or more identical (preferably 95% or more identical, 96% or more identical; 97% or more identical, 98% or more identical, 99% or more identical or 99.5% or more identical).

In some embodiments, nucleic acids encode an antibody light chain comprising a variable domain, the amino acid sequence of which is shown in SEQ ID NO: 11 and an antibody heavy chain comprising a variable domain, the amino acid sequence of which is selected from the group consisting of SEQ ID NO: 13, SEQ ID NO: 15, SEQ ID NO: 17, SEQ ID NO: 19.

In some embodiments, nucleic acid encodes variable domains, the amino acid sequences of which are presented in SEQ ID NO: 11, 13,15,19, which can be used for operable fusion with nucleic acids encoding the corresponding constant domains of antibodies.

Exemplary specific types of nucleic acid molecules of interest are disclosed in more detail below in the experimental section.

As used herein, a nucleic acid molecule is a DNA molecule, such as a genomic DNA molecule or a cDNA molecule, or an RNA molecule, such as an mRNA molecule. In some embodiments, a nucleic acid molecule of the present invention is a DNA (or cDNA) molecule comprising an open reading frame that encodes an antibody or antibody fragment of the present invention and is capable, under suitable conditions (e.g., physiological intracellular conditions), of being used for expression in a heterologous expression system.

In some embodiments, a nucleic acid molecule of the present invention is produced by genetic engineering methods. Methods for producing nucleic acids are well known in the art. For example, the availability of amino acid sequence information or nucleotide sequence information enables preparation of isolated nucleic acid molecules of the present invention by oligonucleotide synthesis. In the case of amino acid sequence information, a number of nucleic acids that differ from each other due to degenerate code may be synthesized. The methods to select codon variants for a desired host are well known in the art.

Synthetic oligonucleotides may be prepared by the phosphoramidite method, and the resultant constructs may be purified according to methods well-known in the art, such as high performance liquid chromatography (HPLC) or other methods as described in, for example, Sambrook et al., Molecular Cloning: A Laboratory Manual, 2nd Ed., (1989) Cold Spring Harbor Press, Cold Spring Harbor, N.Y., and under guidelines described in, e.g., United States Dept. of HHS, National Institute of Health (NIH) Guidelines for Recombinant DNA Research. The long, double-stranded DNA molecules of the present invention may be synthesized in the following manner: by synthesizing several smaller fragments of appropriate complementarity that comprise appropriate termini capable of cohesion with an adjacent fragment. Adjacent fragments may be linked using DNA ligase or PCR-based method.

The nucleic acid molecules of the present invention may be also cloned from biological sources.

The present invention also encompasses nucleic acids that are homologous, substantially the same as, identical to, or derived from nucleic acids encoding polypeptides of the present invention.

The nucleic acids of the invention are present in an environment other than that in which they are present in nature, for example, they are isolated, present in an increased amount, present or expressed in in vitro systems or in cells or organisms other than those in which they are present in natural conditions.

Changes or differences in nucleotide sequence between closely related nucleic acid sequences may represent nucleotide changes in the sequence that arise during the course of normal replication or duplication. Other changes may be specifically designed and introduced into the sequence for specific purposes, such as to change the codons of specific amino acids or a nucleotide sequence in a regulatory region. Such specific changes may be made in vitro using a variety of mutagenesis techniques or obtained in host organisms placed under specific selection conditions that induce or select for the changes. Such specifically generated sequence variants may be referred to as "mutants" or "derivatives" of the original sequence.

Mutant or derivative nucleic acids can be obtained on a template nucleic acid selected from the above nucleic acids by modification, deletion or addition of one or more nucleotides in the template sequence, or a combination thereof, to produce a variant of the template nucleic acid. The modifications, additions or deletions can be performed by any method known in the art (see, e.g., Gustin et al., Biotechniques (1993) 14: 22; Barany, Gene (1985) 37: 111-123; and Colicelli et al., Mol. Gen. Genet. (1985) 199:537-539, Sambrook et al., Molecular Cloning: A Laboratory Manual, (1989), CSH Press, pp. 15.3-15.108) including error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, random mutagenesis, gene reassembly, gene site saturated mutagenesis (GSSM), synthetic ligation reassembly (SLR), or a combination thereof. The modifications, additions or deletions may also be performed by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, and a combination thereof.

Also provided are degenerate variants of nucleic acids that encode the proteins of the present invention. The degenerate variants of nucleic acids include replacements of the codons of nucleic acid with other codons encoding the same amino acids. In particular, the degenerate variants of nucleic acids are generated to increase the expression in a host cell. In this embodiment, the codons of nucleic acid that are non-preferred or less preferred in genes in the host cell are replaced with the codons over-represented in coding sequences in genes in the host cell, wherein said replaced codons encode the same amino acid. Genetic code optimization is well known from the prior art.

The above modifications do not substantially alter the properties of antibodies or functional fragments thereof, but can facilitate protein folding in a host cell, decrease aggregation capacity or modulate other biochemical properties of the proteins, for example, half-life period. In some embodiments, these modifications do not modify biochemical properties of the protein. All types of modifications and mutations specified above are performed at the nucleic acid level.

The claimed nucleic acids may be isolated and prepared in a substantially purified form. A substantially purified form means that the nucleic acids are at least about 50% pure, typically at least about 90% pure and typically are "recombinant", i.e. flanked by one or more nucleotides with which it is not typically associated on a chromosome that occurs in nature in the natural host organism thereof.

Also provided are nucleic acids that encode fusion proteins comprising a protein of the present invention, or fragments thereof, which are discussed in more detail below. The nucleic acids encoding variable domains of the invention can be operatively linked to nucleic acids encoding the corresponding constant domains of the light and heavy chains of the antibody. The nucleic acids encoding the light and heavy chains of an antibody can be operatively linked to nucleic acids encoding a leader peptide that facilitates the transport of expression products from the host cell. The leader peptide is subsequently removed during maturation of the polypeptide.

Also provided are a vector and other nucleic acid constructs comprising the claimed nucleic acids. The term "vector" refers to a nucleic acid molecule capable of transporting another nucleic acid to which it has been operatively linked. Certain vectors can autonomously replicate in host cells to which they were introduced, while other vectors can integrate into host cell genome and replicate together with the host genome. Moreover, some vectors are capable of directing the expression of genes to which they have been operatively linked. Such vectors are called in this application "recombinant expression vectors" (or simply "expression vectors"); exemplary vectors are well known from the prior art. Suitable vectors include viral and non-viral vectors, plasmids, cosmids, phages, etc., preferably plasmids, and are used for cloning, amplifying, expressing, transferring, etc. of a nucleic acid sequence of the present invention to an appropriate host. The choice of appropriate vector is obvious to those skilled in the art. A full-length nucleic acid or a portion thereof is inserted into a vector typically by means of DNA ligase attachment to a cleaved restriction enzyme site in the vector. Alternatively, the desired nucleotide sequence can be inserted by homologous recombination in vivo, typically by attaching regions of homology to the vector on the flanks of the desired nucleotide sequence. Regions of homology are added by ligation of oligonucleotides, or by polymerase chain reaction using primers comprising, for example, both the region of homology and a portion of the desired nucleotide sequence. Typically, the vector has an origin of replication ensuring propagation thereof in host cells as a result of introduction thereof into a cell as an extrachromosomal element. The vector, as a rule, may also comprise regulatory elements ensuring expression of a nucleic acid in the host cell and generation of the target polypeptide. In the expression vector, said nucleic acid is operatively linked to a regulatory sequence that may include promoters, enhancers, terminators, operators, repressors and inducers, as well as a start codon of the polypeptide. In some embodiments, a nucleic acid of the invention is further operatively linked to a leader peptide ensuring the isolation of an expression product from the host cell into the extracellular space.

Also provided are expression cassettes or systems used inter alia for the production of the subject polypeptides (for example, the light and heavy chains of an antibody of the invention) based thereon or for replication of the subject nucleic acid molecules. The expression cassette may exist as an extrachromosomal element or may be integrated into the cell genome as a result of introduction of said expression cassette into the cell. For expression, a protein product encoded by the nucleic acid of the invention is expressed in any convenient expression system, including, for example, bacterial systems, yeast, insects, amphibians, or mammalian cells. In the expression cassette, a target nucleic acid is operatively linked to regulatory sequences that can include promoters, enhancers, terminating sequences, operators, repressors and inducers, as well as a start codon of the polypeptide. In some embodiments, a nucleic acid of the invention is further operatively linked to a leader peptide ensuring the isolation of an expression product from the host cell into the extracellular space. Methods for preparing expression cassettes or systems capable of expressing the desired product are known to those skilled in the art.

The above expression systems may be used in prokaryotic or eukaryotic hosts. Host-cells, such as *E. coli, B. subtilis, S. cerevisiae*, insect cells in combination with baculovirus vectors, or cells of a higher organism, which are not human embryonic cells, such as yeast, plants, vertebrates, e.g., CHO cells (e.g. ATCC CRL-9096), NS0 cells, SP2/0 cells, HEK293 cells, COS cells (e.g. ATCC CRL-1650, CRL-1651) and HeLa (ATCC CCL-2), may be used for production of the protein.

To produce an antibody of the invention, the host cell is co-transformed with an expression vector comprising a nucleic acid encoding an antibody light chain and an expression vector comprising a nucleic acid encoding an antibody heavy chain. In some embodiments, a single expression vector is used, into which nucleic acids encoding both the light and heavy chains of an antibody are introduced.

For expression of light and heavy chains, the expression vector(s) encoding the heavy and light chains are transformed (co-transformed) into a host cell such that the light and heavy chains are expressed in the host cell and preferably are secreted into the medium, in which the host cells are cultured, and from which medium the antibodies can be isolated. Various interpretations of the term "transformation" are intended to include a wide range of methods commonly used for introducing exogenous DNA into a prokaryotic or eukaryotic host cell, for example, electroporation, calcium phosphate precipitation, DEAE-dextran transfection, etc., as described in Sambrook, Fritsch and Maniatis (eds) Molecular Cloning; A Laboratory Manual, Second Edition, Cold Spring Harbor, N.Y. (1989; Ausubel F. M. et al. (eds.) Current Protocols in Molecular Biology, Green Publishing Associates (1989).

When recombinant expression vectors comprising nucleic acids of the antibody are introduced into host cells, the antibodies are generated by culturing the host cells for a period of time sufficient to express the antibody in the host cell, or (more preferably) secrete the antibody into the culture medium, in which the host cells are grown. Antibodies can be isolated from a culture medium using standard protein purification techniques. The cell culture conditions are well known to those skilled in the art and described in Current Protocols in Cell Biology, Bonifacino J. S., Dasso M., Harford J. B., Lippincott-Schwartz J. and Yamada K. M. (eds.) published by John Wiley & Sons, Inc., 2000.

If any of the above host cells or other host cells or organisms suitable for replication and/or expression of the nucleic acids of the invention are used, the resulting replicated nucleic acid, expressed protein or polypeptide are within the scope of the invention as a product of the host cell or organism. The product may be isolated by a suitable technique known in the art.

Cell lines, which stably express the proteins of present invention, can be selected by the methods known in the art (e.g. co-transfection with a selectable marker, such as dhfr, gpt, neomycin, hygromycin, which allows the identification and isolation of the transfected cells that contain the gene integrated into a genome).

The nucleic acid molecules of the present invention may also be used to determine gene expression in a biological sample. A method in which cells are examined for the presence of specific nucleotide sequences, such as genomic DNA or RNA, is well established in the art. Briefly, DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable carrier, e.g. nitrocellulose, nylon, etc., and then probed with a fragment of the subject DNA as a probe. Other techniques, such as oligonucleotide ligation assays, in situ hybridizations, and hybridization to DNA probes immobilized on a solid chip may also find use. Detection of mRNA hybridizing to the subject sequence is indicative of gene expression in the sample.

Therapeutic Use of Antibodies of the Invention

In one aspect, the antibody or active fragment thereof of the present invention is used in the treatment of disorders that are associated with the activity of pathological T lymphocytes bearing the surface TRBV9 family TCRs, for example, exhibiting activity of autoimmune T lymphocytes in AS, celiac disease, T cell lymphomas.

The term "patient", as used in this application, refers to a mammal including but not limited to mice, monkeys, humans, livestock mammals, sports mammals and pet mammals; preferably the term applies to humans. In a particular embodiment, the patient is further characterized by a disease or disorder, or condition, mediated by the presence in the body thereof of TCR, the beta-chain of which belongs to the TRBV9 family. As is known from the prior art, TCR, the beta-chain of which belongs to the TRBV9 family, is associated with AS and celiac disease. Furthermore, TCR, the beta-chain of which belongs to the TRBV9 family, may be associated with the development of a number of blood diseases, such as T cell lymphoma caused by the Epstein-Barr virus.

As used herein, the terms "co-administration", "co-administered" and "in combination with" referring to the antibody with one or more other therapeutic agents, are contemplated to mean, refer to and include the following:

1) the simultaneous administration of such combination of an antibody of the invention and a therapeutic agent to a patient in need of treatment, when such components are formulated together into a single dosage form which releases said components at substantially the same time to said patient, 2) the simultaneous administration of such combination of an antibody of this invention and a therapeutic agent to a patient in need of treatment, when such components are formulated apart from each other into separate dosage forms which are taken at substantially the same time by said patient, whereupon said components are released at substantially the same time to said patient, 3) sequential administration of such combination of an antibody of the invention and a therapeutic agent to a patient in need of treatment, when such components are formulated apart from each other into separate dosage forms which are taken at consecutive times by said patient with a significant time interval between each administration, whereupon said components are released at substantially different times to said patient; and 4) sequential administration of such combination of an antibody of the invention and a therapeutic agent to a patient in need of treatment, when such components are formulated together into a single dosage form which releases said components in a controlled manner whereupon they are concurrently, consecutively, and/or overlappingly released at the same and/or different times to said patient, where each part may be administered by either the same or a different route.

An antibody of the invention (for example, anti-TRBV9-1, anti-TRBV9-2, anti-TRBV9-3 or anti-TRBV9-4) can be administered without further therapeutic treatment, i.e. as an independent therapy. Furthermore, treatment by an antibody of the invention may comprise at least one additional therapeutic treatment (combination therapy). In some embodiments of the invention, the antibody can be co-administered or formulated with another medicament/drug for an autoimmune or oncological disease, the pathogenesis of which involves TCRs comprising the TRBV9 beta-chain, for example, AC, celiac disease, T cell lymphoma, T cell leukemia.

Doses and Routes of Administration

An antibody of the invention will be administered in an amount that is effective in treatment of the condition in question, i.e. in doses and during the periods of time required to achieve the desired result. A therapeutically effective amount may vary according to factors such as the specific condition to be treated, age, sex, and weight of a patient, and whether the antibody is administered alone or in combination with one or more additional immunosuppressive or anti-inflammatory treatment techniques.

Dosage regimens may be adjusted to provide the optimum response. For example, a single bolus may be administered, several divided doses may be administered over time or the dose may be proportionally reduced or increased as indicated by the exigencies of the therapeutic situation. It is especially advantageous to formulate parenteral compositions in a unit dosage form for ease of administration and uniformity of dosage. The unit dosage form as used herein is intended to refer to physically discrete units suited as unitary dosages for patients/subjects to be treated; each unit contains a predetermined quantity of active compound calculated to obtain the desired therapeutic effect in association with the desired pharmaceutical carrier. The specification for the unit dosage forms of the invention is typically dictated by and directly dependent on (a) the unique characteristics of a chemotherapeutic agent and particular therapeutic or prophylactic effect to be achieved, and (b) the limitations inherent in the art of compounding such an active compound for the treatment of sensitivity in the subjects.

Thus, those skilled in the art will recognize from the disclosure herein that dosages and dosage regimens are adjusted in accordance with methods well known in the therapeutic field. This means that a maximum tolerated dose can be easily established, and an effective amount can also be determined that provides a detectable therapeutic effect for the patient, as well as the time requirements for the administration of each agent to achieve a visible therapeutic effect for the patient. Thus, although some doses and dosage regimens are given as examples in this document, these examples in no way limit the dosages and dosage regimens that may be necessary for the patient in the practice of the present invention.

It is to be noted that dosage values may vary with the type and severity of the condition to be alleviated and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the embodied composition. Furthermore, the dosage regimen with the compositions of the present invention can be based on various factors, including the type of a disease, age, weight, gender, patient's health condition, severity of a condition, route of administration and a particular antibody used. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present invention encompasses intra-patient dose-escalation as determined by the person skilled in the art. Determining the required dose and modes are well known in the relevant field of technology and will be clear to the person skilled in the art after becoming acquainted with the ideas disclosed in this document.

Examples of suitable administration methods are provided above.

It is contemplated that a suitable dose of an antibody of the invention will be in the range of 0.1-200 mg/kg, preferably 0.1-100 mg/kg, including about 0.5-50 mg/kg, for example about 1-20 mg/kg. The antibody may be administered, e.g. in a dose of at least 0.25 mg/kg, such as at least 0.5 mg/kg, including at least 1 mg/kg, e.g. at least 1.5 mg/kg, such as at least 2 mg/kg, e.g. at least 3 mg/kg, including at least 4 mg/kg, e.g. at least 5 mg/kg; and for example up to a maximum of 50 mg/kg, including up to a maximum of 30 mg/kg, e.g. up to a maximum of 20 mg/kg, including up to a maximum of 15 mg/kg. The administration will typically be repeated in appropriate time intervals, such as once a week, once every two weeks, once every three weeks or once every four weeks, and for as long as deemed appropriate by a responsible physician, who may, in some cases, increase or reduce the dose if necessary.

Pharmaceutical Composition

The antibody of the invention can be incorporated into a pharmaceutical composition suitable for administration to a patient. The antibodies of the invention may be administered alone or in combination with a pharmaceutically acceptable carrier, diluent, and/or excipients, in single or multiple doses. Pharmaceutical compositions for administration are designed to be appropriate for the selected mode of administration, and pharmaceutically acceptable diluents, carriers, and/or excipients, such as dispersing agents, buffers, surfactants, preservatives, solubilizing agents, isotonicity agents, stabilizing agents and the like be used as appropriate. Said compositions are designed in accordance with conventional methods as in e.g., Remington, The Science and Practice of Pharmacy, 19th Edition, Gennaro, Ed., Mack Publishing Co., Easton, Pa. 1995, which provides various techniques for obtaining the compositions as are generally known to practitioners.

"Medicament (drug)"—is a compound or a mixture of compounds as a pharmaceutical composition in the form of tablets, capsules, powders, lyophilisates, injections, infusion, ointments and other ready forms intended for restoration, improvement or modification of physiological functions in humans and animals, and for treatment and preventing of diseases, for diagnostics, anesthesia, contraception, cosmetology and others. Any method for administering peptides, proteins or antibodies accepted in the art may be suitably employed for an antibody of the invention.

The term "pharmaceutically acceptable" refers to one or more compatible liquid or solid components that are suitable for administration in a mammal, preferably a human.

The term "excipient" is used herein to describe any ingredient other than the above ingredients of the invention. These are substances of inorganic or organic nature which are used in the pharmaceutical manufacturing in order to give drug products the necessary physicochemical properties.

The term "buffer", "buffer composition", "buffering agent" refers to a solution, which is capable of resisting changes in pH by the action of its acid-base conjugate components, and which allows the antibody drug to resist changes in pH. Generally, the pharmaceutical composition preferably has a pH in the range from 4.0 to 8.0. Examples of buffers used include, but are not limited to, acetate, phosphate, citrate, histidine, succinate, etc. buffer solutions.

The terms "tonic agent", "osmolyte" or "osmotic agent", as used herein, refer to an excipient that can increase the osmotic pressure of a liquid antibody formulation. "Isotonic" drug is a drug that has an osmotic pressure equivalent to that of human blood. Isotonic drugs typically have an osmotic pressure from about 250 to 350 mOsm/kg. Isotonic agents used include, but are not limited to, polyols, saccharides and sucrose, amino acids, metal salts, for example, sodium chloride, etc.

"Stabilizer" refers to an excipient or a mixture of two or more excipients that provide the physical and/or chemical stability of the active agent. Stabilizers include amino acids, for example, but are not limited to, arginine, histidine, glycine, lysine, glutamine, proline; surfactants, for example, but are not limited to, polysorbate 20 (trade name: Tween 20), polysorbate 80 (trade name: Tween 80), polyethylene-polypropylene glycol and copolymers thereof (trade names:

Poloxamer, Pluronic, sodium dodecyl sulfate (SDS); antioxidants, for example, but are not limited to, methionine, acetylcysteine, ascorbic acid, monothioglycerol, sulfurous acid salts, etc.; chelating agents, for example, but are not limited to, ethylenediaminetetraacetic acid (EDTA), diethylenetriaminepentaacetic acid (DTPA), sodium citrate, etc.

A pharmaceutical composition is "stable" if the active agent retains physical stability and/or chemical stability and/or biological activity thereof during the specified shelf life at storage temperature, for example, of 2-8° C. Preferably, the active agent retains both physical and chemical stability, as well as biological activity. Storage period is adjusted based on the results of stability test in accelerated or natural aging conditions.

A pharmaceutical composition comprising a monoclonal antibody of the invention may be administered to a patient exhibiting pathologies as described in this application using standard administration methods, including peroral, intravenous, intraperitoneal, subcutaneous, pulmonary, transdermal, intramuscular, intranasal, buccal, sublingual, or suppository administration.

The pharmaceutical composition of the invention preferably comprises or is a "therapeutically effective amount" of an antibody of the invention. The term "therapeutically effective amount" is intended to refer to an amount that is effective at dosages and for periods of time necessary to achieve the desired therapeutic result. A therapeutically effective amount of an antibody may vary according to factors such as disease state, age, sex, and weight of a subject, and the ability of an antibody or part thereof to elicit a desired response in a subject. A therapeutically effective amount is also one in which any toxic or detrimental effects are outweighed by the therapeutically beneficial effects of the antibody. "Prophylactically effective amount" is intended to refer to the amount that is effective at dosages and for periods of time necessary to achieve the desired prophylactic result. Since a prophylactic dose is prescribed for individuals before or at an early stage of disease, typically a prophylactically effective amount may be less than a therapeutically effective amount.

A therapeutically effective or prophylactically effective amount is at least a minimal therapeutically beneficial dose that is less than the toxic dose of an active agent necessary to provide therapeutic benefit to the patient. On the other hand, a therapeutically effective amount of an antibody of the invention is an amount that reduces, in mammals, preferably humans, the biological activity of autoimmune clones, for example, through binding TCR, the beta-chain of which belongs to the TRBV9 family, where the presence of said clones causes or contributes to undesirable pathological effects, or decreasing TCR, the beta-chain of which belongs to the TRBV9 family, causes a beneficial therapeutic effect in a mammal, preferably a human.

The route of administration of an antibody of the invention can be oral, parenteral, inhalation or local. Preferably, the antibodies of the invention can be included in a pharmaceutical composition acceptable for parenteral administration. The term "parenteral" as used herein includes intravenous, intramuscular, subcutaneous, rectal, vaginal or intraperitoneal administration. Intravenous, intraperitoneal or subcutaneous injections are preferred routes of administration. Acceptable pharmaceutical carriers for such injections are well known from the prior art.

As described in appropriate guidelines, the pharmaceutical compositions shall be sterile and stable under the conditions of production and storage in a container, which is provided by, for example, hermetically sealed vials (ampoules) or syringes. Thus, the pharmaceutical compositions can be subjected to filtration sterilization after preparing the composition, or can be made microbiologically suitable by any other technique. A typical composition for an intravenous infusion can include 250-1000 ml of fluid such as sterile Ringer's solution, physiologic saline, dextrose solution or Hank's salt solution, and a therapeutically effective dose (for example, 1-100 mg/ml or more) of an antibody concentrate. The doses may vary depending on disease type and severity. It is well known from the state of medical art that doses for any of patients depend on multiple factors including patient's sizes, body surface area, age, specific compound to be administered, gender, duration and route of administration, general health state and other simultaneously administered medications. A typical dose can be, for example, in a range of 0.001-1000 μg; however, doses lower and higher than this illustrative range are anticipated, especially given the abovementioned parameters. The daily parenteral dosing regimen may be from 0.1 μg/kg to 100 μg/kg of overall body weight, preferably from 0.3 μg/kg to 10 μg/kg, and more preferably from 1 μg/kg to 1 μg/kg, even more preferably from 0.5 to 10 μg/kg of body weight per day. The treatment process can be monitored by periodical assessment of patient's health state. For repeated administration for several days or longer, depending on patient's condition, the treatment is repeated until the desired response or suppression of symptoms of a disease. However, another dosing regimens not described herein can also be applied. The desired dosage can be administered by single-pole administration, multiple bolus administrations, or by continuous infusion of the antibody, depending on the pharmacokinetic disintegration sample that the practitioner wants to achieve.

Said assumed properties of an antibody largely depend on a physician's decision. The key factor in choosing the appropriate dose and regimen is the desired result. The factors considered herein include a certain disease to be treated, a certain mammal to receive the treatment, clinical condition of a certain patient, disorder cause, antibody administration site, specific antibody type, route of administration, administration regimen and other factors well known in the medical arts.

The therapeutic agents of the invention can be frozen or lyophilized and reconstituted in an appropriate sterile carrier prior to administration. Freeze-drying and reconstitution can result in some loss of antibody's activity. Doses can be adjusted to compensate this loss. Generally, pH between 6 and 8 is preferred for a pharmaceutical composition.

Article of Manufacture (Products) and Kits

A further embodiment of the invention is an article of manufacture that comprises products used to treat autoimmune diseases and related conditions and malignant blood diseases, the pathogenesis of which involves TCRs bearing the TRBV9 family beta-chain. Such diseases include, for example, AS, celiac disease, T cell leukemia, T cell lymphoma and others.

The product is a container with a label and package insert, which can be in a blister and/or package. Suitable containers include, e.g., vials, ampoules, syringes, etc. The containers may be made of various materials such as glass or polymer material. The container comprises a composition which is effective for treating a certain condition and can have a sterile access port. At least one active ingredient in the composition is an antibody according to the invention. The label and package insert indicates that the drug is intended to be used to treat a certain condition. The label and/or package insert additionally contain instructions for administering the antibody composition in a patient, including indications, frequency, dose, route of administration, contraindications and/or precautions for such therapeutic products. In one embodiment, the package insert indicates that the composition is intended to be used for treating.

Furthermore, an article of manufacture may comprise, without limitation, other products necessary for commercial purposes or necessary for a consumer, such as solvents, diluents, filters, needles and syringes.

The invention also relates to kits that can be used for various purposes, for example, for assessment of the ability to kill T cells bearing the TRBV9 family TCRs, for purification or immunoprecipitation of the TRBV9 receptor from cells. For isolation and purification, the kit may comprise an antibody coupled to granules (e.g., sepharose granules). The kit comprises a container, a label and a package insert.

Diagnostic Use

Antibodies of the invention are also used in diagnostic purposes (e.g., in vitro, ex vivo). For example, an antibody can be used for detecting or measuring the level of T lymphocytes comprising TRBV9 family TCRs in samples obtained from a patient (e.g., tissue sample or a sample of body fluid, such as an inflammatory exudate, blood, intestinal fluid, saliva or urine). Suitable methods for detection and measurement include immunoassays, such as flow cytometry, enzyme-linked immunosorbent assay (ELISA), chemiluminescent assay, radioimmunoassay, and immunohistology. The invention further includes kits, for example, diagnostic kits comprising antibodies described herein.

In order that this invention may be better understood, the following examples are set forth. These examples are for purposes of illustration only and are not to be construed as limiting the scope of the invention in any manner.

All publications, patents, and patent applications cited in this specification are incorporated herein by reference. Although the above invention has been described in some detail by way of illustration and example in order to avoid ambiguous interpretation, it will be quite clear to those skilled in the art based on the ideas disclosed in this invention that certain changes and modifications can be made without deviating from the essence or scope of the appended embodiments.

Experimental Section

Example 1. Production and Purification of Antibody

Nucleic acids (SEQ ID NO: 10, 12, 14, 16, 18) encoding the variable domains of antibody heavy and light chains were obtained by amplifying DNA fragments using overlapping primers and high-fidelity Q5 polymerase (NEB, USA). The obtained nucleic acids were purified on columns from Quagen (Germany) using a reagent kit (#28104) and targetedly cloned into commercially available pFuse vectors comprising constant regions of human heavy (IgG1) and light (kappa) chain genes (Invivogen, USA). The sequences of the cloned fragments were confirmed by sequencing using the Sanger method.

As a result, plasmids comprising coding sequences for four antibody heavy chain variants were obtained:

HV anti-TRBV9-1, the nucleotide and amino acid sequences of which are shown in SEQ ID NO: 20 and 21;

HV anti-TRBV9-2, the nucleotide and amino acid sequences of which are shown in SEQ ID NO: 22 and 23;

HV anti-TRBV9-3, the nucleotide and amino acid sequences of which are shown in SEQ ID NO: 24 and 25;

HV anti-TRBV9-3, the nucleotide and amino acid sequences of which are shown in SEQ ID NO: 26 and 27;

and for one antibody light chain variant, LV anti-TRBV9, (SEQ ID NO: 28 and 29).

The degree of humanization of antibody heavy chain is 72%, and that of light chain is 69%.

To obtained antibodies, plasmids were transfected into HEK293F suspension cell line. 293fectine reagent (Thermo Fisher scientific, USA #1234701) was used for transfection. 30 million cells were placed in each 30 ml of FreeStyle medium, 30 μg of pFuse plasmid encoding one of antibody heavy chain variants, and 30 μg of pFuse plasmid encoding antibody light chain and 60 μl of 293fectine (Thermo Fisher scientific, USA #12347019) were added thereto. Plasmids comprising immunoglobulin heavy and light chains were dissolved in water tested for endotoxin content (Quagen, USA).

The resulting reaction mixtures were incubated at 37° C. on a shaker for a week. One week later, the cell supernatant was harvested, which was used to isolate antibodies. To this end, the supernatant was centrifuged three times at 10,000 rpm for 10 min, and the liquid fraction was purified using a 1 ml HiTrap PrG column (Thermo Fisher scientific, USA). For elution, 0.1 M glycine buffer, pH2.5, was used, brought in HCl. Isolation quality was evaluated using 12% PAGE under denaturing conditions. Quantification was performed by measurement on NanoDrop2000 microspectrophotometer at 280A. The resulting product was stored at +4° C.

Table 1 shows the characteristics of isolated proteins.

TABLE 1

Characteristics of antibodies

| Name | Molecular weight (theor.), kDa | Isoelectric point | Extinction coefficent | Protein purity, % | Protein concentration, mg/ml | Absorbation at 400 nm, 1 = 1 cm |
|---|---|---|---|---|---|---|
| TRBV9-1 | 146.3 | 8.35 | 1.52 | 98.3 | 2.58 | 0.005 |
| TRBV9-2 | 146.5 | 8.35 | 1.52 | 98.7 | 1.91 | 0.003 |
| TRBV9-3 | 146.5 | 8.35 | 1.52 | 97.8 | 1.83 | 0.003 |
| TRBV9-4 | 146.5 | 8.35 | 1.52 | 98.9 | 1.56 | 0.004 |

The affinity of anti-TRBV9 antibodies was measured using OctetRed 96 instrument (from ForteBio). Antigens (Table 1) were non-specifically immobilized on the surface of amine reactive second-generation sensors (from AR2G) according to the standard protocol described in the manufacturer's manual in regard to preparation and immobilization of AR2G sensors. Analysis was conducted at 30° C. using phosphate-buffered saline (PBS) comprising 0.1% Tween-20 and 0.1% BSA as a working buffer. Binding affinity of anti-TRBV9 antibodies was analyzed using a working buffer from a concentration of 126 nM to 2 nM with an increment of 2. The binding curves, after subtracting a reference signal, were analyzed using Octet Data Analysis software (Version 7.0) in accordance with the standard procedure and using 1:1 interaction model. The results are summarized in Table 2.

ng/µl, as well as a monoclonal antibody against CD3-eFluor405 ((OKT3 clone, eBioscience);) at a concentration recommended by the manufacturer, were added in each test to an aliquot of mononuclear fraction each comprising 500,000 cells (per test).

The resulting reaction mixtures having a volume of 50 µl of PBS supplemented with 0.5% BSA, 2 mM EDTA were incubated at room temperature for 30 min, after which the cells were washed with PBS buffer supplemented with 0.5% BSA, 2 mM EDTA, and the results of staining were analyzed by flow cytometry (FACSARIA III, USA, FIG. 1-4). It was shown that all resulting variants of monoclonal antibodies specifically recognize the fraction of CD3+positive cells. However, the TRBV9-2 variant showed the most stable staining, which was 2.9% of the CD3-positive fraction, at both antibody concentrations of 5 ng/µl and 0.5 ng/µl.

TABLE 2

Evaluation of antibody affinity

| | Antigen: TRBV9 + TRAV26 | | | | Antigen: TRBV9 + TRAV38 | | | |
|---|---|---|---|---|---|---|---|---|
| | kD, M | kon, 1/Ms | kdis, 1/s | R2 | kD, M | kon, 1/Ms | kdis, 1/s | R2 |
| TRBV9-1 | 2.20E−10 | 5.15E+05 | 1.13E−04 | 0.9915 | 4.14E−10 | 4.41E+05 | 1.83E−04 | 0.9815 |
| | 2.78E−10 | 6.58E+05 | 1.83E−04 | 0.99 | 3.65E−10 | 5.62E+05 | 2.05E−04 | 0.9776 |
| | 2.04E−10 | 5.59E+05 | 1.14E−04 | 0.9841 | 5.29E−10 | 3.71E+05 | 1.96E−04 | 0.9877 |
| TRBV9-2 | 1.35E−11 | 4.47E+05 | 6.02E−06 | 0.9905 | <1.0E−12 | 3.97E+05 | <1.0E−07 | 0.9772 |
| | <1.0E−12 | 3.81E+05 | <1.0E−07 | 0.9861 | <1.0E−12 | 2.89E+05 | <1.0E−07 | 0.9894 |
| TRBV9-3 | 3.19E−10 | 2.87E+05 | 9.16E−05 | 0.9991 | 3.11E−10 | 3.09E+05 | 9.61E−05 | 0.9942 |
| | 5.82E−10 | 1.68E+05 | 9.80E−05 | 0.9998 | 4.00E−10 | 2.29E+05 | 9.16E−05 | 0.9962 |
| TRBV9-4 | <1.0E−12 | 8.65E+05 | <1.0E−07 | 0.9381 | <1.0E−12 | 7.13E+05 | <1.0E−07 | 0.9058 |
| | <1.0E−12 | 5.79E+05 | <1.0E−07 | 0.9546 | <1.0E−12 | 4.76E+05 | <1.0E−07 | 0.9512 |

No interaction with antibodies was observed when using TRBV7+TRAV38 antigens. TRBV9-2 and TRBV9-4 antibodies exhibited the best characteristics.

Example 2. Use of Anti-TRBV9 Monoclonal Antibodies for Labeling T Lymphocytes Expressing TCR Beta-Chain Belonging to TRBV9 Family Monoclonal antibodies (anti-TRBV9-1, anti-TRBV9-2, anti-TRBV9-3, anti-TRBV9-4, characterized in the heavy chain CDR3 sequence) were produced as described in Example 1. To visualize the antibodies, they were labeled with fluorescein using fluorescein isothiocyanate reagent (Sigma, USA) according to the manufacturer's protocol. The amount of fluorophores that reacted with antibody molecules was controlled by absorption spectrum ratio at wavelengths of 495/280 nm. Labeled antibodies were used to detect T lymphocytes expressing the TCR beta-chain of the TRBV9 family in the mononuclear fraction of human blood.

The peripheral blood of 5 healthy donors was used to obtain this fraction. Blood was collected in EDTA Vacuette tubes (2×9 ml each), the mononuclear fraction was isolated according to the standard procedure described in (Kovalchuk L. V. et al. Immunology: Workshop—2010.—176 p.). After isolation, the cells were transferred to phosphate buffered saline (PBS) comprising 0.5% bovine serum albumin (BSA) and 2 mM EDTA. The total number of cells and viability thereof was determined by trypan blue staining method as described by Lang N. R. (Stimulation of lymphocytes M.: Medicine, 1976.-288 p.).

To label T lymphocytes, anti-TRBV9-1, anti-TRBV9-2, anti-TRBV9-3, anti-TRBV9-4 antibodies in PBS buffer supplemented with 0.5% bovine serum albumin (BSA) and 2 Mm EDTA, to a final concentration of 5 ng/µl and 0.5

Whereas other antibody variants (anti-TRBV9-2, anti-TRBV9-3, anti-TRBV9-4) showed staining of a different proportion of TRBV9+ lymphocytes at the same concentrations. Also, the specificity of anti-TRBV9-2 was determined by the absence of weakly stained non-specific CD3-negative cells, which are present when using other variants, and by a significant separation of specific cell population from other CD3-positive lymphocytes being negative for TRBV9.

Thus, it was found that the second variant (anti-TRBV9-2) exhibits the most effective and highly specific staining of TRBV9+T lymphocytes. This antibody can be used for diagnostic purposes for the detection of TRBV9+T lymphocytes at a concentration of 0.6 ng/µl.

To assess the specificity of anti-TRBV9-1, anti-TRBV9-2, anti-TRBV9-3, anti-TRBV9-4 antibodies, mononuclear blood fractions obtained as described above from 5 peripheral blood samples were stained with anti-TRBV9-FITC antibody and anti-CD3-eFluor450 (eBioscience, USA) antibody as described above, using the following ratios:

5 µl (1 µg) of anti-CD3-eFluor 450 (eBioscience, USA) and 30 ng (0.5 ng/µl) of anti-TRBV9-2 FITC were added to 3 million cells of mononuclear blood fraction. The reaction mixtures were incubated at room temperature for 30 min, the cells were washed with PBS buffer supplemented with 0.5% BSA and sorted on a cell sorter (FACSARIA III, USA) to isolate a population of CD3+TRBV9+ cells, as well as CD3+TRBV9− cells. Sorting quality was controlled by resorting of CD3+TRBV9+ population, which resorting showed 95% enrichment of the target cell population.

The obtained cell fractions were placed in RLT buffer (Quagen, Germany), RNA was isolated therefrom using Quiagen RNAeasy mini kit #217004 reagent kit (Quagen) according to the manufacturer's protocol. CDNA was synthesized on isolated RNA template, fragments of T receptor beta-chain were amplified according to the protocol described in Britanova et al (3 Immunol, 2016, 196(12) 5005-5013) using Mint cDNA synthesis kit (Eurogen, Russia). The Illumina adapters (USA) were ligated to the produced amplicons, sequencing was performed on MiSeq Illumina platform according to the sequencer manufacturer's protocol. Sequencing data were analyzed using MiGEC, MiXCR and VDJtools software. Data analysis showed that 90% of sequences from CD3+TRBV9+fraction belong to the TRBV9 beta-chain variable segment gene family. At the same time, no fragments containing a TRBV9 variable segment sequence were found in the CD3+TRBV9- fraction. Thus, anti-TRBV9-1, anti-TRBV9-2, anti-TRBV9-3, anti-TRBV9-4 specifically bind to the TRBV9 family beta-chain.

Example 3. Functional Activity of Antibodies

Monoclonal antibodies (anti-TRBV9-1, anti-TRBV9-2, anti-TRBV9-3, anti-TRBV9-4, characterized in the heavy chain CDR3 sequence) were obtained as described in Example 1. The mononuclear fraction of human blood was obtained as described in Example 2.

Further, natural killer cells were isolated from a portion of mononuclear fraction using human NK cells isolation reagent kit #130-092-657 (Miltenyi biotec, USA). The manufacturers' protocol was used. The quality of NK cell isolation was assessed by cytofluometry (BD FACS ARIA III, USA) using labeled antibodies CD16-FITC, CD56-PE, CD3-VioBlue. The enrichment with NK cells was 85-95%.

To assess cytotoxicity, antibodies (anti-TRBV9-1, anti-TRBV9-2, anti-TRBV9-3, or anti-TRBV9-4) were added to an aliquot of mononuclear fraction comprising 1×106 cells to a final concentration of 5 µg/ml. Antibodies Remicade at the same concentration as anti-TRBV9 antibodies were used as a negative control. No antibodies were added to the control cell aliquot (positive control). Also, 105 NK cells were added to all reaction mixtures. The final reaction volume was 100 µl.

The reaction mixtures were incubated at room temperature for one hour, the cells were then washed several times to remove antibodies and distributed into the wells of a 96-well round-bottom plate, on a table.

Figure 5:
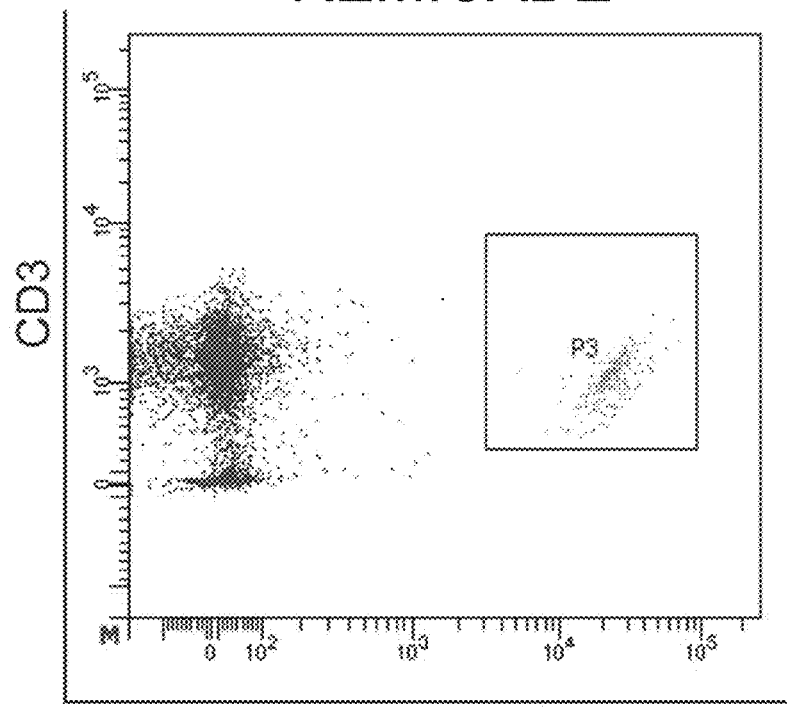
FIG. 5 shows two-parameter histograms of distribution of mononuclear blood fraction cells using an anti-CD3 monoclonal antibody (ordinate axis) labeled with eFluor 405 and monoclonal antibodies against TRBV9 (abscissa axis) labeled with FITC following cytotoxicity test: incubation with anti-TRBV9-2 (test) and Remicade (control).
Figure 5:
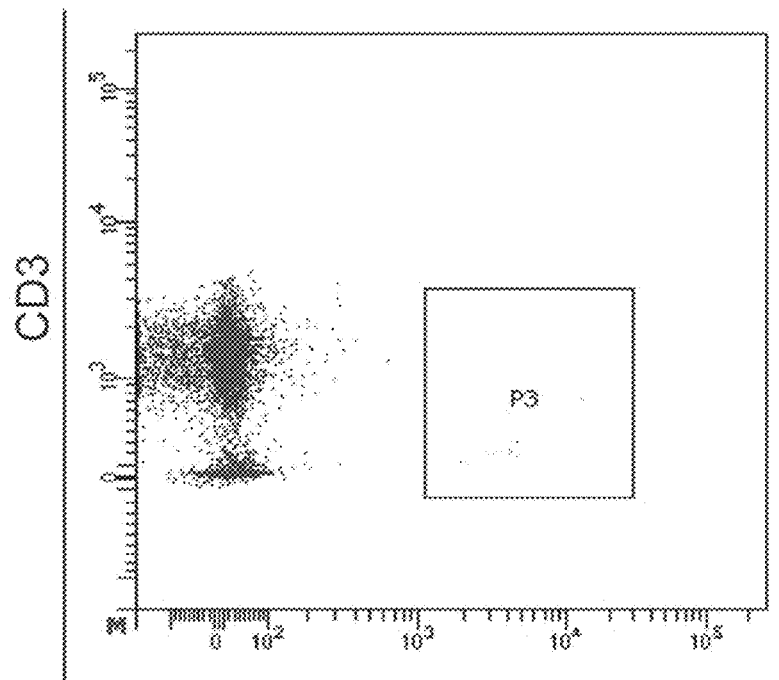

After 6 days, the cells were harvested from the wells and used for immunophenotypic analysis using flow cytometry. The following antibodies were used to detect T lymphocytes: anti-CD3-eFluor450 (OKT3 clone, eBioscience); anti-CD8-PC7 (SFCI21Thy2D3 clone, Beckman Coulter, USA); the resulting antibodies are anti-TRBV9-1,2,3,4 labeled with Fitc. After staining, the cells were washed and analyzed on BD FACSARIA III instrument. No CD3+ TRBV9+T-lymphocytes were detected in samples incubated with anti-TRBV9 antibodies of the present invention. In contrast, CD3+TRBV9+ double positive T lymphocytes are still detected in the control sample with no anti-TRBV9 antibody ("zero control"), as well as with therapeutic antibodies Remicade, which fact confirms specific elimination of TRBV9+ T cells following addition of antibodies against TRBV9. FIG. 5 shows a typical result of flow cytometry. In a further negative control, where non-cytotoxic anti-CD6 antibodies were used instead of anti-TRBV9 antibodies of the present invention, no changes were observed in the target CD3+CD6+ population as compared to "zero control". This indicates that no screening of the epitope by unlabeled antibodies on Day 6 is observed, and confirms the ability of anti-TRBV9 antibodies to eliminate cells bearing the TRBV9 family TCR.

Example 4. Engineering of Stable Cell Line

A stable cell line producing anti-TRBV9-2 monoclonal antibody was obtained by transfecting suspension CHO-S cell line with vector constructs that comprised the optimum ratio of light and heavy antibody chains. Clonal lines maintaining a high level (more than 100 mg/L) were obtained using ClonePix robotic platform (Molecular Devices). Productivity of selected clones was analyzed by Biomek FX robotics automated system (Beckman Coulter), and Octet RED96 analytical system (Pall Life Sciences). Producer was cultured using serum-free media which do not contain animal-derived protein. BCD085 product for preclinical studies was produced in HyClone single-use bioreactor (Thermoscientific) 200 L fermenter.

Example 5. Obtaining a Pharmaceutical Composition Comprising Antibody of the Invention The pharmaceutical composition's components are shown in Table 3.

TABLE 3

Concentrations of pharmaceutical composition's components

| Component | Concentration |
|---|---|
| Anti-TRBV9-2 antibody | 10-50 mg/ml |
| 10 mM citrate buffer to pH | 6.0-7.0 |
| Sodium chloride | 50-150 mM |
| Sucrose, trehalose | 0.3-0.5% |
| Water for injections | up to 1 ml. |

Example 6. Kit Comprising Pharmaceutical Composition with Antibodies

To produce kits with a dosage form comprising an anti-TRBV9-2 antibody composition, the pharmaceutical composition prepared according to Example 5 is sealed in 1 ml ampoules or syringes under sterile conditions, labeled and packaged into plastic or cardboard containers.

Also, an insert is included in the ampoule container.

Example 7. Variants of Antibodies According to the Invention

Mutant HV anti-TRBV9-1 sequences were obtained by site-directed mutagenesis using "overlap extention" of PCR products as described by Wurch et al., Methods in Molecular Biology. 12 (9), 653-657 (2004). Q5 high-fidelity polymerase (NEB, USA) was used for PCR, according to the manufacturer's guidelines. After amplification, the obtained fragments were purified by 1% agarose gel electrophoresis and further extraction. Gel-isolated DNA fragments comprising mutations were combined into a complete construct by overlap extention PCR (denaturation at 95° C. for 12 sec; annealing at 55° C. for 2 min; extention at 72° C. for 1 min, 8 PCR cycles). This method assumes that fragments, which are present in the reaction mixture, having regions complementary to each other are used as a template and primer. The entire construct was amplified by standard PCR with the addition of primers complementary to the ends of the amplified fragment. The obtained nucleic acids were purified on Quagen (Germany) columns using a reagent kit (#28104) and cloned into pFuse vector as described in Example 1. The mutant DNA sequences were checked by sequencing according to the Sanger method. The nucleotide and amino acid sequences of the resulting variable domains are shown as follows: variant 1—in SEQ ID NO: 30 and SEQ ID NO: 31; variant 2—in SEQ ID NO: 32 and SEQ ID NO: 33. The ability of mutant antibodies to bind to T lymphocytes expressing the TCR beta-chain belonging to the TRBV9 family was validated as described in Example 2. It was shown that the introduced substitutions do not affect the binding specificity.

What is claimed is:

1. A monoclonal antibody or antigen-binding fragment thereof that specifically binds to the TRBV9 (T Cell Receptor Beta Variable 9) family beta chain region of human T cell receptor, comprising:
   1) a heavy chain variable domain comprising HCDR1, HCDR2 and HCDR3, where
      the HCDR 1 comprises the amino acid sequence of SEQ ID NO: 1,
      the HCDR 2 comprises the amino acid sequence of SEQ ID NO: 2,
      the HCDR 3 comprises the amino acid sequence selected from the group of SEQ ID NO: 3, SEQ ID NO: 4, SEQ ID NO: 5, and SEQ ID NO: 6; and
   2) a light chain variable domain comprising LCDR1, LCDR2 and LCDR3, where
      the LCDR 1 comprises the amino acid sequence of SEQ ID NO: 7,
      the LCDR 2 comprises the amino acid sequence of SEQ ID NO: 8, and
      the LCDR 3 comprises the amino acid sequence of SEQ ID NO: 9.

2. The monoclonal antibody or antigen-binding fragment thereof according to claim 1, wherein the heavy chain variable domain comprises an amino acid sequence that is at least 90% identical to an amino acid sequence selected from the group of SEQ ID NO: 13, SEQ ID NO: 15, SEQ ID NO: 17, and SEQ ID NO: 19.

3. The monoclonal antibody or antigen-binding fragment thereof according to claim 2, wherein the heavy chain variable domain comprises an amino acid sequence selected from the group of SEQ ID NO: 13, SEQ ID NO: 15, SEQ ID NO: 17, and SEQ ID NO: 19.

4. The monoclonal antibody or antigen-binding fragment thereof according to claim 1, wherein the light chain variable domain comprises an amino acid sequence that is at least 90% identical to the amino acid sequence shown in SEQ ID NO: 11.

5. The monoclonal antibody or antigen-binding fragment thereof according to claim 4, wherein the light chain variable domain comprises the amino acid sequence of SEQ ID NO: 11.

6. The monoclonal antibody or antigen-binding fragment thereof according to claim 1, comprising:
 1) A heavy chain having an amino acid sequence that is at least 90% identical to a sequence selected from the group SEQ ID NO: 21, SEQ ID NO: 23, SEQ ID NO: 25, and SEQ ID NO: 27; and
 2) A light chain having an amino acid sequence that is at least 90% identical to the sequence of SEQ ID NO: 29.

7. The monoclonal antibody of claim 6, comprising:
 1) A heavy chain comprising an amino acid sequence selected from the group of SEQ ID NO: 21, SEQ ID NO: 23, SEQ ID NO: 25, and SEQ ID NO: 27; and
 2) A light chain comprising the amino acid sequence of SEQ ID NO: 29.

8. The monoclonal antibody according to claim 1, wherein the antibody is a full-length IgG antibody.

9. A nucleic acid that encodes an antibody or antigen-binding fragment thereof according to claim 1, which specifically binds to the TRBV9 family beta chain region of human T cell receptor.

10. An expression vector comprising the nucleic acid according to claim 9.

11. A host cell for obtaining an antibody or antigen-binding fragment thereof according to claim 1, comprising a nucleic add that encodes the antibody or antigen-binding fragment thereof.

12. A method of obtaining an antibody or antigen-binding fragment thereof according to claim 1, comprising cultivating a host cell that comprises a nucleic add that encodes the antibody or antigen-binding fragment thereof in culture medium under conditions that ensure the production of the antibody, followed by isolation and purification of the obtained antibody.

13. A pharmaceutical composition comprising the antibody or antigen-binding fragment thereof according to claim 1, in combination with one or several pharmaceutically acceptable excipients.

* * * * *

UNITED STATES PATENT AND TRADEMARK OFFICE
CERTIFICATE OF CORRECTION

PATENT NO. : 11,597,767 B2
APPLICATION NO. : 16/957328
DATED : March 7, 2023
INVENTOR(S) : Olga Vladimirovna Britanova et al.

It is certified that error appears in the above-identified patent and that said Letters Patent is hereby corrected as shown below:

In the Claims

In Column 64, Claim 11, Line 13, delete "add" and insert -- acid --, therefor.

In Column 64, Claim 12, Line 17, delete "add" and insert -- acid --, therefor.

Signed and Sealed this
Second Day of January, 2024

*Katherine Kelly Vidal*
Katherine Kelly Vidal
*Director of the United States Patent and Trademark Office*

```
                          SEQUENCE LISTING

<160> NUMBER OF SEQ ID NOS: 33

<210> SEQ ID NO 1
<211> LENGTH: 5
<212> TYPE: PRT
<213> ORGANISM: Artificial
<220> FEATURE:
<223> OTHER INFORMATION: HCDR1 amino acid sequence (according to the
      Kabat numbering scheme)

<400> SEQUENCE: 1

Asp Tyr Leu Val His
1               5

<210> SEQ ID NO 2
<211> LENGTH: 17
<212> TYPE: PRT
<213> ORGANISM: Artificial
<220> FEATURE:
<223> OTHER INFORMATION: HCDR2 amino acid sequence (according to the
      Kabat numbering scheme)

<400> SEQUENCE: 2

Trp Ile Asn Thr Tyr Thr Gly Thr Pro Thr Tyr Ala Asp Asp Phe Glu
1               5                   10                  15

Gly

<210> SEQ ID NO 3
<211> LENGTH: 13
<212> TYPE: PRT
<213> ORGANISM: Artificial
<220> FEATURE:
<223> OTHER INFORMATION: HCDR3 amino acid sequence (according to the
      Kabat numbering scheme)

<400> SEQUENCE: 3

Ser Trp Arg Arg Gly Leu Arg Gly Leu Gly Phe Asp Tyr
1               5                   10

<210> SEQ ID NO 4
<211> LENGTH: 13
<212> TYPE: PRT
<213> ORGANISM: artificial
<220> FEATURE:
<223> OTHER INFORMATION: HCDR3 amino acid sequence (according to the
      Kabat numbering scheme)

<400> SEQUENCE: 4

Ser Trp Arg Arg Gly Leu Arg Gly Ile Gly Phe Asp Tyr
1               5                   10

<210> SEQ ID NO 5
<211> LENGTH: 13
<212> TYPE: PRT
<213> ORGANISM: Artificial
<220> FEATURE:
<223> OTHER INFORMATION: HCDR3 amino acid sequence (according to the
      Kabat numbering scheme)

<400> SEQUENCE: 5

Ser Trp Arg Arg Gly Ile Arg Gly Leu Gly Phe Asp Tyr
1               5                   10
```

<210> SEQ ID NO 6
<211> LENGTH: 13
<212> TYPE: PRT
<213> ORGANISM: Artificial
<220> FEATURE:
<223> OTHER INFORMATION: HCDR3 amino acid sequence (according to the
      Kabat numbering scheme)

<400> SEQUENCE: 6

Ser Trp Arg Arg Gly Ile Arg Gly Ile Gly Phe Asp Tyr
1               5                   10

<210> SEQ ID NO 7
<211> LENGTH: 11
<212> TYPE: PRT
<213> ORGANISM: Artificial
<220> FEATURE:
<223> OTHER INFORMATION: LCDR1 amino acid sequence (according to the
      Kabat numbering scheme)

<400> SEQUENCE: 7

Lys Ala Ser Lys Ser Ile Asn Lys Tyr Leu Ala
1               5                   10

<210> SEQ ID NO 8
<211> LENGTH: 7
<212> TYPE: PRT
<213> ORGANISM: Artificial
<220> FEATURE:
<223> OTHER INFORMATION: LCDR2 amino acid sequence (according to the
      Kabat numbering scheme)

<400> SEQUENCE: 8

Asp Gly Ser Thr Leu Gln Ser
1               5

<210> SEQ ID NO 9
<211> LENGTH: 9
<212> TYPE: PRT
<213> ORGANISM: Artificial
<220> FEATURE:
<223> OTHER INFORMATION: LCDR3 amino acid sequence (according to the
      Kabat numbering scheme)

<400> SEQUENCE: 9

Gln Gln His Asn Glu Tyr Pro Pro Thr
1               5

<210> SEQ ID NO 10
<211> LENGTH: 321
<212> TYPE: DNA
<213> ORGANISM: Artificial
<220> FEATURE:
<223> OTHER INFORMATION: The nucleotide sequence of the antibody light
      chain variable domain

<400> SEQUENCE: 10
gacgtgcaga tgacccagtc cccctacaac ctggccgcct ccccggcga gtccgtgtcc        60 atcaactgca aggcctccaa gtccatcaac aagtacctgg cctggtacca gcagaagccc      120
ggcaagccca caagctgct gatctacgac ggctccaccc tgcagtccgg catcccctcc       180
aggttctccg gctccggctc cggcaccgac ttcaccctga ccatcagggg cctggagccc      240
gaggacttcg cctgtacta ctgccagcag cacaacgagt accccccac cttcggcgcc       300 ggcaccaagc tggagctgaa g                                                321

<210> SEQ ID NO 11
<211> LENGTH: 107
<212> TYPE: PRT
<213> ORGANISM: Artificial
<220> FEATURE:
<223> OTHER INFORMATION: The amino acid sequence of the antibody light
    chain variable domain

<400> SEQUENCE: 11

Asp Val Gln Met Thr Gln Ser Pro Tyr Asn Leu Ala Ala Ser Pro Gly
1               5                   10                  15

Glu Ser Val Ser Ile Asn Cys Lys Ala Ser Lys Ser Ile Asn Lys Tyr
            20                  25                  30

Leu Ala Trp Tyr Gln Gln Lys Pro Gly Lys Pro Asn Lys Leu Leu Ile
        35                  40                  45

Tyr Asp Gly Ser Thr Leu Gln Ser Gly Ile Pro Ser Arg Phe Ser Gly
    50                  55                  60

Ser Gly Ser Gly Thr Asp Phe Thr Leu Thr Ile Arg Gly Leu Glu Pro
65                  70                  75                  80

Glu Asp Phe Gly Leu Tyr Tyr Cys Gln Gln His Asn Glu Tyr Pro Pro
                85                  90                  95

Thr Phe Gly Ala Gly Thr Lys Leu Glu Leu Lys
            100                 105

<210> SEQ ID NO 12
<211> LENGTH: 366
<212> TYPE: DNA
<213> ORGANISM: Artificial
<220> FEATURE:
<223> OTHER INFORMATION: The nucleotide sequence of the antibody heavy
    chain variable domain

<400> SEQUENCE: 12
cagatccagc tggtgcagtc cggccccgag ctgagggagc ccggcgagtc cgtgaagctg      60
tcctgcaagg cctccggcta caccttcacc gactacctgg tgcactgggt gaagcaggcc     120
cccggcaagg gcctgaagtg gatgggctgg atcaacacct acaccggcac ccccacctac     180
gccgacgact cgagggcag gttcgtgttc tccctggagg cctccgcctc caccgccaac     240
ctgcagatct ccaacctgaa gaacgaggac accgccacct acttctgcgc caggtcctgg     300 aggagggggcc tgaggggcct gggcttcgac tactggggcc agggcgtgtt cgtgaccgtg     360
tcctcc                                                               366

<210> SEQ ID NO 13
<211> LENGTH: 122
<212> TYPE: PRT
<213> ORGANISM: Artificial
<220> FEATURE:
<223> OTHER INFORMATION: The amino acid sequence of the antibody heavy
    chain variable domain

<400> SEQUENCE: 13

Gln Ile Gln Leu Val Gln Ser Gly Pro Glu Leu Arg Glu Pro Gly Glu
1               5                   10                  15

Ser Val Lys Leu Ser Cys Lys Ala Ser Gly Tyr Thr Phe Thr Asp Tyr
            20                  25                  30

Leu Val His Trp Val Lys Gln Ala Pro Gly Lys Gly Leu Lys Trp Met
        35                  40                  45

Gly Trp Ile Asn Thr Tyr Thr Gly Thr Pro Thr Tyr Ala Asp Asp Phe

```
                    50                  55                  60

Glu Gly Arg Phe Val Phe Ser Leu Glu Ala Ser Ala Ser Thr Ala Asn
 65                  70                  75                  80

Leu Gln Ile Ser Asn Leu Lys Asn Glu Asp Thr Ala Thr Tyr Phe Cys
                    85                  90                  95

Ala Arg Ser Trp Arg Arg Gly Leu Arg Gly Leu Gly Phe Asp Tyr Trp
                100                 105                 110

Gly Gln Gly Val Phe Val Thr Val Ser Ser
            115                 120

<210> SEQ ID NO 14
<211> LENGTH: 366
<212> TYPE: DNA
<213> ORGANISM: Artificial
<220> FEATURE:
<223> OTHER INFORMATION: The nucleotide sequence of the antibody heavy
      chain variable domain

<400> SEQUENCE: 14
cagatccagc tggtgcagtc cggccccgag ctgagggagc ccggcgagtc cgtgaagctg      60
tcctgcaagg cctccggcta caccttcacc gactacctgg tgcactgggt gaagcaggcc     120
cccggcaagg gcctgaagtg gatgggctgg atcaacacct acaccggcac ccccacctac     180
gccgacgact cgagggcag gttcgtgttc tccctggagg cctccgcctc caccgccaac     240
ctgcagatct ccaacctgaa gaacgaggac accgccacct acttctgcgc caggtcctgg     300
aggaggggcc tgaggggcat cggcttcgac tactggggcc agggcgtgtt cgtgaccgtg     360
tcctcc                                                                366

<210> SEQ ID NO 15
<211> LENGTH: 122
<212> TYPE: PRT
<213> ORGANISM: Artificial
<220> FEATURE:
<223> OTHER INFORMATION: The amino acid sequence of the antibody heavy
      chain variable domain

<400> SEQUENCE: 15

Gln Ile Gln Leu Val Gln Ser Gly Pro Glu Leu Arg Glu Pro Gly Glu
  1               5                  10                  15

Ser Val Lys Leu Ser Cys Lys Ala Ser Gly Tyr Thr Phe Thr Asp Tyr
                20                  25                  30

Leu Val His Trp Val Lys Gln Ala Pro Gly Lys Gly Leu Lys Trp Met
            35                  40                  45

Gly Trp Ile Asn Thr Tyr Thr Gly Thr Pro Thr Tyr Ala Asp Asp Phe
 50                  55                  60

Glu Gly Arg Phe Val Phe Ser Leu Glu Ala Ser Ala Ser Thr Ala Asn
 65                  70                  75                  80

Leu Gln Ile Ser Asn Leu Lys Asn Glu Asp Thr Ala Thr Tyr Phe Cys
                85                  90                  95

Ala Arg Ser Trp Arg Arg Gly Leu Arg Gly Ile Gly Phe Asp Tyr Trp
                100                 105                 110

Gly Gln Gly Val Phe Val Thr Val Ser Ser
            115                 120

<210> SEQ ID NO 16
<211> LENGTH: 366
<212> TYPE: DNA
<213> ORGANISM: Artificial
```

```
<220> FEATURE:
<223> OTHER INFORMATION: The nucleotide sequence of the antibody heavy
      chain variable domain

<400> SEQUENCE: 16
cagatccagc tggtgcagtc cggccccgag ctgagggagc cggcgagtc cgtgaagctg      60 tcctgcaagg cctccggcta caccttcacc gactacctgg tgcactgggt gaagcaggcc    120
cccggcaagg gcctgaagtg gatgggctgg atcaacacct acaccggcac ccccacctac    180
gccgacgact cgagggcag gttcgtgttc tccctggagg cctccgcctc caccgccaac    240
ctgcagatct ccaacctgaa gaacgaggac accgccacct acttctgcgc caggtcctgg    300
aggaggggca tcaggggcct gggcttcgac tactggggcc agggcgtgtt cgtgaccgtg    360
tcctcc                                                              366

<210> SEQ ID NO 17
<211> LENGTH: 122
<212> TYPE: PRT
<213> ORGANISM: Artificial
<220> FEATURE:
<223> OTHER INFORMATION: The amino acid sequence of the antibody heavy
      chain variable domain

<400> SEQUENCE: 17

Gln Ile Gln Leu Val Gln Ser Gly Pro Glu Leu Arg Glu Pro Gly Glu
 1               5                  10                  15

Ser Val Lys Leu Ser Cys Lys Ala Ser Gly Tyr Thr Phe Thr Asp Tyr
             20                  25                  30

Leu Val His Trp Val Lys Gln Ala Pro Gly Lys Gly Leu Lys Trp Met
         35                  40                  45

Gly Trp Ile Asn Thr Tyr Thr Gly Thr Pro Thr Tyr Ala Asp Asp Phe
     50                  55                  60

Glu Gly Arg Phe Val Phe Ser Leu Glu Ala Ser Ala Ser Thr Ala Asn
 65                  70                  75                  80

Leu Gln Ile Ser Asn Leu Lys Asn Glu Asp Thr Ala Thr Tyr Phe Cys
                 85                  90                  95

Ala Arg Ser Trp Arg Arg Gly Ile Arg Gly Leu Gly Phe Asp Tyr Trp
            100                 105                 110

Gly Gln Gly Val Phe Val Thr Val Ser Ser
        115                 120

<210> SEQ ID NO 18
<211> LENGTH: 366
<212> TYPE: DNA
<213> ORGANISM: Artificial
<220> FEATURE:
<223> OTHER INFORMATION: The nucleotide sequence of the antibody heavy
      chain variable domain

<400> SEQUENCE: 18
cagatccagc tggtgcagtc cggccccgag ctgagggagc cggcgagtc cgtgaagctg      60 tcctgcaagg cctccggcta caccttcacc gactacctgg tgcactgggt gaagcaggcc    120
cccggcaagg gcctgaagtg gatgggctgg atcaacacct acaccggcac ccccacctac    180
gccgacgact cgagggcag gttcgtgttc tccctggagg cctccgcctc caccgccaac    240
ctgcagatct ccaacctgaa gaacgaggac accgccacct acttctgcgc caggtcctgg    300
aggaggggca tcaggggcat cggcttcgac tactggggcc agggcgtgtt cgtgaccgtg    360
tcctcc                                                              366
```

<210> SEQ ID NO 19
<211> LENGTH: 122
<212> TYPE: PRT
<213> ORGANISM: Artificial
<220> FEATURE:
<223> OTHER INFORMATION: The amino acid sequence of the antibody heavy
      chain variable domain

<400> SEQUENCE: 19

Gln Ile Gln Leu Val Gln Ser Gly Pro Glu Leu Arg Glu Pro Gly Glu
1               5                   10                  15

Ser Val Lys Leu Ser Cys Lys Ala Ser Gly Tyr Thr Phe Thr Asp Tyr
            20                  25                  30

Leu Val His Trp Val Lys Gln Ala Pro Gly Lys Gly Leu Lys Trp Met
        35                  40                  45

Gly Trp Ile Asn Thr Tyr Thr Gly Thr Pro Thr Tyr Ala Asp Asp Phe
    50                  55                  60

Glu Gly Arg Phe Val Phe Ser Leu Glu Ala Ser Ala Ser Thr Ala Asn
65                  70                  75                  80

Leu Gln Ile Ser Asn Leu Lys Asn Glu Asp Thr Ala Thr Tyr Phe Cys
                85                  90                  95

Ala Arg Ser Trp Arg Arg Gly Ile Arg Gly Ile Gly Phe Asp Tyr Trp
            100                 105                 110

Gly Gln Gly Val Phe Val Thr Val Ser Ser
        115                 120

<210> SEQ ID NO 20
<211> LENGTH: 1365
<212> TYPE: DNA
<213> ORGANISM: Artificial
<220> FEATURE:
<223> OTHER INFORMATION: The nucleotide sequence of the anti-TRBV9-1
      antibody heavy chain

<400> SEQUENCE: 20
cagatccagc tggtgcagtc cggccccgag ctgagggagc ccggcgagtc cgtgaagctg      60
tcctgcaagg cctccggcta caccttcacc gactacctgg tgcactgggt gaagcaggcc     120
cccggcaagg gcctgaagtg gatgggctgg atcaacacct acaccggcac ccccacctac     180
gccgacgact cgagggcag gttcgtgttc tccctgagg cctccgcctc caccgccaac      240
ctgcagatct ccaacctgaa gaacgaggac accgccacct acttctgcgc caggtcctgg     300
aggaggggcc tgaggggcct gggcttcgac tactgggggcc agggcgtgtt cgtgaccgtg     360
tcctccgcct ccaccaaggg cccatcggtc ttccccctgg caccctcctc caagagcacc     420
tctgggggca gcgcggccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgactgtgc cctctagcag cttgggcacc     600
cagacctaca tctgcaacgt gaatcacaag cccagcaaca ccaaggtgga caagaaagtt     660
gagcccccga aatcttgtga caaaactcac acatgcccac cgtgcccagc acctgaactc     720
ctggggggac cgtcagtctt cctcttcccc ccaaaaccca aggacaccct catgatctcc     780
cggacccctg aggtcacatg cgtggtggtg gacgtgagcc acgaagaccc tgaggtcaag     840
ttcaactggt acgtggacgg cgtggaggtg cataatgcca agacaaagcc gcgggaggag     900
cagtacaaca gcacgtaccg tgtggtcagc gtcctcaccg tcctgcacca ggactggctg     960

```
aatggcaagg agtacaagtg caaggtctcc aacaaagccc tcccagcccc catcgagaaa    1020
accatctcca agccaaagg gcagcccga gaaccacagg tgtacaccct gccccatcc       1080 cgggatgagc tgaccaagaa ccaggtcagc ctgacctgcc tggtcaaagg cttctatccc    1140
agcgacatcg ccgtggagtg ggagagcaat gggcagccgg agaacaacta caagaccacg    1200
cctcccgtgc tggactccga cggctccttc ttcctctaca gcaagctcac cgtggacaag    1260
agcaggtggc agcaggggaa cgtcttctca tgctccgtga tgcatgaggc tctgcacaac    1320
cactacacgc agaagagcct ctccctgtct ccgggtaaat gataa                   1365
```

<210> SEQ ID NO 21
<211> LENGTH: 452
<212> TYPE: PRT
<213> ORGANISM: Artificial
<220> FEATURE:
<223> OTHER INFORMATION: The amino acid sequence of the anti-TRBV9-1
      antibody heavy chain

<400> SEQUENCE: 21

```
Gln Ile Gln Leu Val Gln Ser Gly Pro Glu Leu Arg Glu Pro Gly Glu
1               5                   10                  15

Ser Val Lys Leu Ser Cys Lys Ala Ser Gly Tyr Thr Phe Thr Asp Tyr
            20                  25                  30

Leu Val His Trp Val Lys Gln Ala Pro Gly Lys Gly Leu Lys Trp Met
        35                  40                  45

Gly Trp Ile Asn Thr Tyr Thr Gly Thr Pro Thr Tyr Ala Asp Asp Phe
    50                  55                  60

Glu Gly Arg Phe Val Phe Ser Leu Glu Ala Ser Ala Ser Thr Ala Asn
65                  70                  75                  80

Leu Gln Ile Ser Asn Leu Lys Asn Glu Asp Thr Ala Thr Tyr Phe Cys
                85                  90                  95

Ala Arg Ser Trp Arg Gly Leu Arg Gly Leu Gly Phe Asp Tyr Trp
            100                 105                 110

Gly Gln Gly Val Phe Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285
```

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Arg Asp Glu Leu Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro Gly Lys
    450

<210> SEQ ID NO 22
<211> LENGTH: 1365
<212> TYPE: DNA
<213> ORGANISM: Artificial
<220> FEATURE:
<223> OTHER INFORMATION: The nucleotide sequence of the anti-TRBV9-2
      antibody heavy chain

<400> SEQUENCE: 22
cagatccagc tggtgcagtc cggccccgag ctgagggagc ccggcgagtc cgtgaagctg      60
tcctgcaagg cctccggcta caccttcacc gactacctgg tgcactgggt gaagcaggcc     120
cccggcaagg gcctgaagtg gatgggctgg atcaacacct acaccggcac ccccacctac     180
gccgacgact cgagggcag gttcgtgttc tccctggagg cctccgcctc caccgccaac     240
ctgcagatct ccaacctgaa gaacgaggac accgccacct acttctgcgc caggtcctgg     300
aggaggggcc tgaggggcat cggcttcgac tactggggcc agggcgtgtt cgtgaccgtg     360
tcctccgcct ccaccaaggg cccatcggtc ttccccctgg cacctcctc caagagcacc     420 tctgggggca gcgcggccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgactgtgc cctctagcag cttgggcacc     600
cagacctaca tctgcaacgt gaatcacaag cccagcaaca ccaaggtgga caagaaagtt     660
gagcccccga atcttgtga caaaactcac acatgcccac cgtgcccagc acctgaactc     720
ctggggggac cgtcagtctt cctcttcccc ccaaaaccca aggacaccct catgatctcc     780
cggacccctg aggtcacatg cgtggtggtg gacgtgagcc acgaagaccc tgaggtcaag     840
ttcaactggt acgtggacgg cgtggaggtg cataatgcca agacaaagcc gcgggaggag     900
cagtacaaca gcacgtaccg tgtggtcagc gtcctcaccg tcctgcacca ggactggctg     960
aatggcaagg agtacaagtg caaggtctcc aacaaagccc tcccagcccc catcgagaaa    1020
accatctcca aagccaaagg gcagccccga gaaccacagg tgtacaccct gcccccatcc    1080

```
cgggatgagc tgaccaagaa ccaggtcagc ctgacctgcc tggtcaaagg cttctatccc   1140
agcgacatcg ccgtggagtg ggagagcaat gggcagccgg agaacaacta caagaccacg   1200
cctcccgtgc tggactccga cggctccttc ttcctctaca gcaagctcac cgtggacaag   1260
agcaggtggc agcaggggaa cgtcttctca tgctccgtga tgcatgaggc tctgcacaac   1320
cactacacgc agaagagcct ctccctgtct ccgggtaaat gataa                    1365
```

```
<210> SEQ ID NO 23
<211> LENGTH: 452
<212> TYPE: PRT
<213> ORGANISM: Artificial
<220> FEATURE:
<223> OTHER INFORMATION: The amino acid sequence of the anti-TRBV9-2
      antibody heavy chain

<400> SEQUENCE: 23
```

```
Gln Ile Gln Leu Val Gln Ser Gly Pro Glu Leu Arg Glu Pro Gly Glu
1               5                   10                  15

Ser Val Lys Leu Ser Cys Lys Ala Ser Gly Tyr Thr Phe Thr Asp Tyr
            20                  25                  30

Leu Val His Trp Val Lys Gln Ala Pro Gly Lys Gly Leu Lys Trp Met
        35                  40                  45

Gly Trp Ile Asn Thr Tyr Thr Gly Thr Pro Thr Tyr Ala Asp Asp Phe
    50                  55                  60

Glu Gly Arg Phe Val Phe Ser Leu Glu Ala Ser Ala Ser Thr Ala Asn
65                  70                  75                  80

Leu Gln Ile Ser Asn Leu Lys Asn Glu Asp Thr Ala Thr Tyr Phe Cys
                85                  90                  95

Ala Arg Ser Trp Arg Arg Gly Leu Arg Gly Ile Gly Phe Asp Tyr Trp
            100                 105                 110

Gly Gln Gly Val Phe Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300
```

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 24
<211> LENGTH: 1365
<212> TYPE: DNA
<213> ORGANISM: Artificial
<220> FEATURE:
<223> OTHER INFORMATION: The nucleotide sequence of the anti-TRBV9-3
      antibody heavy chain

<400> SEQUENCE: 24
cagatccagc tggtgcagtc cggccccgag ctgagggagc ccggcgagtc cgtgaagctg     60
tcctgcaagg cctccggcta caccttcacc gactacctgg tgcactgggt gaagcaggcc    120
cccggcaagg gcctgaagtg gatgggctgg atcaacacct acaccggcac ccccacctac    180
gccgacgact cgagggcag gttcgtgttc tccctggagg cctccgcctc caccgccaac    240
ctgcagatct ccaacctgaa gaacgaggac accgccacct acttctgcgc caggtcctgg    300
aggaggggca tcaggggcct gggcttcgac tactggggcc agggcgtgtt cgtgaccgtg    360
tcctccgcct ccaccaaggg cccatcggtc ttccccctgg cacctcctc aagagcacc    420 tctgggggca gcggccct gggctgcctg gtcaaggact acttccccga accggtgacg    480
gtgtcgtgga actcaggcgc cctgaccagc ggcgtgcaca ccttcccggc tgtcctacag    540
tcctcaggac tctactccct cagcagcgtg gtgactgtgc cctctagcag cttgggcacc    600
cagacctaca tctgcaacgt gaatcacaag cccagcaaca ccaaggtgga caagaaagtt    660 gagccccga atcttgtga caaaactcac acatgcccac cgtgcccagc acctgaactc    720
ctggggggac cgtcagtctt cctcttcccc ccaaaaccca aggacaccct catgatctcc    780
cggacccctg aggtcacatg cgtggtggtg gacgtgagcc acgaagaccc tgaggtcaag    840
ttcaactggt acgtggacgg cgtggaggtg cataatgcca agacaaagcc gcggaggag    900 cagtacaaca gcacgtaccg tgtggtcagc gtcctcaccg tcctgcacca ggactggctg    960
aatggcaagg agtacaagtg caaggtctcc aacaaagccc tcccagcccc catcgagaaa   1020
accatctcca agccaaagg gcagcccga gaaccacagg tgtacaccct gcccccatcc   1080
cgggatgagc tgaccaagaa ccaggtcagc ctgacctgcc tggtcaaagg cttctatccc   1140

-continued

```
agcgacatcg ccgtggagtg ggagagcaat gggcagccgg agaacaacta caagaccacg    1200
cctcccgtgc tggactccga cggctccttc ttcctctaca gcaagctcac cgtggacaag    1260
agcaggtggc agcaggggaa cgtcttctca tgctccgtga tgcatgaggc tctgcacaac    1320
cactacacgc agaagagcct ctccctgtct ccgggtaaat gataa                    1365
```

<210> SEQ ID NO 25
<211> LENGTH: 452
<212> TYPE: PRT
<213> ORGANISM: Artificial
<220> FEATURE:
<223> OTHER INFORMATION: The amino acid sequence of the anti-TRBV9-3 antibody heavy chain

<400> SEQUENCE: 25

```
Gln Ile Gln Leu Val Gln Ser Gly Pro Glu Leu Arg Glu Pro Gly Glu
1               5                   10                  15

Ser Val Lys Leu Ser Cys Lys Ala Ser Gly Tyr Thr Phe Thr Asp Tyr
            20                  25                  30

Leu Val His Trp Val Lys Gln Ala Pro Gly Lys Gly Leu Lys Trp Met
        35                  40                  45

Gly Trp Ile Asn Thr Tyr Thr Gly Thr Pro Thr Tyr Ala Asp Asp Phe
    50                  55                  60

Glu Gly Arg Phe Val Phe Ser Leu Glu Ala Ser Ala Ser Thr Ala Asn
65                  70                  75                  80

Leu Gln Ile Ser Asn Leu Lys Asn Glu Asp Thr Ala Thr Tyr Phe Cys
                85                  90                  95

Ala Arg Ser Trp Arg Arg Gly Ile Arg Gly Leu Gly Phe Asp Tyr Trp
            100                 105                 110

Gly Gln Gly Val Phe Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320
```

```
Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 26
<211> LENGTH: 1365
<212> TYPE: DNA
<213> ORGANISM: Artificial
<220> FEATURE:
<223> OTHER INFORMATION: The nucleotide sequence of the anti-TRBV9-4
      antibody heavy chain

<400> SEQUENCE: 26
cagatccagc tggtgcagtc cggccccgag ctgagggagc ccggcgagtc cgtgaagctg      60
tcctgcaagg cctccggcta caccttcacc gactacctgg tgcactgggt gaagcaggcc    120
cccggcaagg gcctgaagtg gatgggctgg atcaacacct acaccggcac ccccacctac    180
gccgacgact cgagggcag gttcgtgttc tccctggagg cctccgcctc caccgccaac    240
ctgcagatct ccaacctgaa gaacgaggac accgccacct acttctgcgc caggtcctgg    300
aggaggggca tcaggggcat cggcttcgac tactgggggcc agggcgtgtt cgtgaccgtg    360
tcctccgcct ccaccaaggg cccatcggtc ttccccctgg caccctcctc caagagcacc    420
tctgggggca gcggccct gggctgcctg gtcaaggact acttccccga accggtgacg    480
gtgtcgtgga actcaggcgc cctgaccagc ggcgtgcaca ccttcccggc tgtcctacag    540
tcctcaggac tctactccct cagcagcgtg gtgactgtgc cctctagcag cttgggcacc    600
cagacctaca tctgcaacgt gaatcacaag cccagcaaca ccaaggtgga caagaaagtt    660 gagccccga atcttgtga caaaactcac acatgccccac cgtgcccagc acctgaactc    720
ctggggggac cgtcagtctt cctcttcccc ccaaaaccca aggacaccct catgatctcc    780
cggacccctg aggtcacatg cgtggtggtg gacgtgagcc acgaagaccc tgaggtcaag    840
ttcaactggt acgtggacgg cgtggaggtg cataatgcca agacaaagcc gcgggaggag    900
cagtacaaca gcacgtaccg tgtggtcagc gtcctcaccg tcctgcacca ggactggctg    960
aatggcaagg agtacaagtg caaggtctcc aacaaagccc tcccagcccc catcgagaaa   1020
accatctcca aagccaaagg gcagccccga gaaccacagg tgtacaccct gcccccatcc   1080
cgggatgagc tgaccaagaa ccaggtcagc ctgacctgcc tggtcaaagg cttctatccc   1140
agcgacatcg ccgtggagtg ggagagcaat gggcagccgg agaacaacta caagaccacg   1200
cctcccgtgc tggactccga cggctccttc ttcctctaca gcaagctcac cgtggacaag   1260
```

```
agcaggtggc agcaggggaa cgtcttctca tgctccgtga tgcatgaggc tctgcacaac    1320
cactacacgc agaagagcct ctccctgtct ccgggtaaat gataa                    1365
```

<210> SEQ ID NO 27
<211> LENGTH: 452
<212> TYPE: PRT
<213> ORGANISM: Artificial
<220> FEATURE:
<223> OTHER INFORMATION: The amino acid sequence of the anti-TRBV9-4
      antibody heavy chain

<400> SEQUENCE: 27

```
Gln Ile Gln Leu Val Gln Ser Gly Pro Glu Leu Arg Glu Pro Gly Glu
1               5                   10                  15

Ser Val Lys Leu Ser Cys Lys Ala Ser Gly Tyr Thr Phe Thr Asp Tyr
            20                  25                  30

Leu Val His Trp Val Lys Gln Ala Pro Gly Lys Gly Leu Lys Trp Met
        35                  40                  45

Gly Trp Ile Asn Thr Tyr Thr Gly Thr Pro Thr Tyr Ala Asp Asp Phe
    50                  55                  60

Glu Gly Arg Phe Val Phe Ser Leu Glu Ala Ser Ala Ser Thr Ala Asn
65                  70                  75                  80

Leu Gln Ile Ser Asn Leu Lys Asn Glu Asp Thr Ala Thr Tyr Phe Cys
                85                  90                  95

Ala Arg Ser Trp Arg Gly Ile Arg Gly Ile Gly Phe Asp Tyr Trp
            100                 105                 110

Gly Gln Gly Val Phe Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335
```

```
Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro Gly Lys
    450

<210> SEQ ID NO 28
<211> LENGTH: 639
<212> TYPE: DNA
<213> ORGANISM: Artificial
<220> FEATURE:
<223> OTHER INFORMATION: The nucleotide sequence of the anti-TRBV9
      antibody light chain

<400> SEQUENCE: 28
gacgtgcaga tgacccagtc cccctacaac ctggccgcct cccccggcga gtccgtgtcc      60
atcaactgca aggcctccaa gtccatcaac aagtacctgg cctggtacca gcagaagccc     120
ggcaagccca caagctgct gatctacgac ggctccaccc tgcagtccgg catccccctcc     180 aggttctccg gctccggctc cggcaccgac ttcaccctga ccatcagggg cctggagccc     240
gaggacttcg cctgtacta ctgccagcag cacaacgagt accccccac cttcggcgcc      300 ggcaccaagc tggagctgaa gcgaactgtg gctgcaccat ctgtcttcat cttcccgcca     360
tctgatgagc agttgaaatc tggaactgcc tctgtcgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgtcctcgc ccgtcacaaa gagcttcaac aggggagag                           639

<210> SEQ ID NO 29
<211> LENGTH: 214
<212> TYPE: PRT
<213> ORGANISM: Artificial
<220> FEATURE:
<223> OTHER INFORMATION: The amino acid sequence of the anti-TRBV9
      antibody light chain

<400> SEQUENCE: 29

Asp Val Gln Met Thr Gln Ser Pro Tyr Asn Leu Ala Ala Ser Pro Gly
1               5                   10                  15

Glu Ser Val Ser Ile Asn Cys Lys Ala Ser Lys Ser Ile Asn Lys Tyr
            20                  25                  30

Leu Ala Trp Tyr Gln Gln Lys Pro Gly Lys Pro Asn Lys Leu Leu Ile
        35                  40                  45

Tyr Asp Gly Ser Thr Leu Gln Ser Gly Ile Pro Ser Arg Phe Ser Gly
    50                  55                  60
```

Ser Gly Ser Gly Thr Asp Phe Thr Leu Thr Ile Arg Gly Leu Glu Pro
65                  70                  75                  80

Glu Asp Phe Gly Leu Tyr Tyr Cys Gln Gln His Asn Glu Tyr Pro Pro
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 30
<211> LENGTH: 333
<212> TYPE: DNA
<213> ORGANISM: Artificial
<220> FEATURE:
<223> OTHER INFORMATION: The nucleotide sequence of the variant of the
      antibody heavy chain variable domain

<400> SEQUENCE: 30
cagatccagt tggtgcagtc cggccccgag ctgaaggagc ccggcgagtc cgtgaagatc      60
tcctgcaagg cctccggcta caccttcacc gactacctgg tgcactgggt gaagcaggcc     120
cccggcaagg gcatcaagtg gatgggctgg atcaacacct acaccggcac ccccacctac     180
gccgacgact cgagggcag gttcgtgttc tccatcgagg cctccgcctc caccgccaac     240
ctgcagatct ccaacatcaa gaacgaggac accgccacct acttctgcgc caggtcctgg     300
aggaggggcc tgagggggcct gggcttcgac tac                                 333

<210> SEQ ID NO 31
<211> LENGTH: 111
<212> TYPE: PRT
<213> ORGANISM: Artificial
<220> FEATURE:
<223> OTHER INFORMATION: The amino acid sequence of the variant of the
      antibody heavy chain variable domain

<400> SEQUENCE: 31

Gln Ile Gln Leu Val Gln Ser Gly Pro Glu Leu Lys Glu Pro Gly Glu
1               5                   10                  15

Ser Val Lys Ile Ser Cys Lys Ala Ser Gly Tyr Thr Phe Thr Asp Tyr
                20                  25                  30

Leu Val His Trp Val Lys Gln Ala Pro Gly Lys Gly Ile Lys Trp Met
            35                  40                  45

Gly Trp Ile Asn Thr Tyr Thr Gly Thr Pro Tyr Ala Asp Asp Phe
        50                  55                  60

Glu Gly Arg Phe Val Phe Ser Ile Glu Ala Ser Ala Ser Thr Ala Asn
65                  70                  75                  80

```
Leu Gln Ile Ser Asn Ile Lys Asn Glu Asp Thr Ala Thr Tyr Phe Cys
                85                  90                  95

Ala Arg Ser Trp Arg Arg Gly Leu Arg Gly Leu Gly Phe Asp Tyr
            100                 105                 110

<210> SEQ ID NO 32
<211> LENGTH: 333
<212> TYPE: DNA
<213> ORGANISM: Artificial
<220> FEATURE:
<223> OTHER INFORMATION: The nucleotide sequence of the variant of the
      antibody heavy chain variable domain

<400> SEQUENCE: 32
cagatccagt tggtgcagtc cggccccgag ataaaggagc ccggcgagtc cgtgaagatc        60
tcctgcaagg cctccggcta caccttcacc gactacctgg tgcactgggt gaagcaggcc       120
cccggcaagg gcatcaagtg gatgggctgg atcaacacct acaccggcac ccccacctac       180
gccgacgact cgagggcag gttcgtgttc tccatcgagg cctccgcctc caccgccaac       240
ctgcagatct ccaacatcaa gaacgaggac accgccacct acttctgcgc caggtcctgg       300
aggaggggcc tgaggggcct gggcttcgac tac                                    333

<210> SEQ ID NO 33
<211> LENGTH: 111
<212> TYPE: PRT
<213> ORGANISM: Artificial
<220> FEATURE:
<223> OTHER INFORMATION: The amino acid sequence of the variant of the
      antibody heavy chain variable domain

<400> SEQUENCE: 33

Gln Ile Gln Leu Val Gln Ser Gly Pro Glu Ile Lys Glu Pro Gly Glu
1               5                   10                  15

Ser Val Lys Ile Ser Cys Lys Ala Ser Gly Tyr Thr Phe Thr Asp Tyr
                20                  25                  30

Leu Val His Trp Val Lys Gln Ala Pro Gly Lys Gly Ile Lys Trp Met
            35                  40                  45

Gly Trp Ile Asn Thr Tyr Thr Gly Thr Pro Thr Tyr Ala Asp Asp Phe
    50                  55                  60

Glu Gly Arg Phe Val Phe Ser Ile Glu Ala Ser Ala Ser Thr Ala Asn
65              70                  75                  80

Leu Gln Ile Ser Asn Ile Lys Asn Glu Asp Thr Ala Thr Tyr Phe Cys
                85                  90                  95

Ala Arg Ser Trp Arg Arg Gly Leu Arg Gly Leu Gly Phe Asp Tyr
            100                 105                 110
```